(12) United States Patent
Kogure et al.

(10) Patent No.: US 12,059,532 B2
(45) Date of Patent: Aug. 13, 2024

(54) CONTROL APPARATUS

(71) Applicant: Paramount Bed Co., Ltd., Tokyo (JP)

(72) Inventors: Takamasa Kogure, Tokyo (JP); Masato Shimokawa, Tokyo (JP); Yuji Hosokawa, Tokyo (JP); Toshihide Shiino, Tokyo (JP)

(73) Assignee: Paramount Bed Co., Ltd., Tokyo (JP)

( * ) Notice: Subject to any disclaimer, the term of this patent is extended or adjusted under 35 U.S.C. 154(b) by 719 days.

(21) Appl. No.: 16/925,810

(22) Filed: Jul. 10, 2020

(65) Prior Publication Data

US 2021/0106785 A1   Apr. 15, 2021

(30) Foreign Application Priority Data

Oct. 11, 2019   (JP) ................. 2019-188189

(51) Int. Cl.
*A61M 21/02* (2006.01)
*A61B 5/00* (2006.01)
*G08B 21/22* (2006.01)

(52) U.S. Cl.
CPC ........... *A61M 21/02* (2013.01); *A61B 5/4806* (2013.01); *G08B 21/22* (2013.01)

(58) Field of Classification Search
CPC .............. A61M 21/02; A61M 2205/18; A61M 2205/332; A61M 2205/3375; A61M 2205/3569; A61M 2230/42; A61M 2021/0044; A61M 2021/0083; A61M 2230/06; A61B 5/4806; A61B 5/0205; A61B 5/1036; A61B 5/1116; A61B 5/4815; A61B 5/6892; A61B 5/024; A61B 5/0816; A61B 5/1118; A61B 5/4809; A61B 5/6802; A61B 5/6803; A61B 5/6804;

(Continued)

(56) References Cited

U.S. PATENT DOCUMENTS

2004/0103475 A1\* 6/2004 Ogawa ................. A61G 7/057
5/613
2006/0104071 A1\* 5/2006 Parsons ................. F21V 21/26
362/404

(Continued)

FOREIGN PATENT DOCUMENTS

JP   S63-222711 A   9/1988
JP   H07-225042 A   8/1995

(Continued)

OTHER PUBLICATIONS

NPL16925810_JP2008010274_EnglishTranslation which is Machine Translation of JP2008010274A , Tonegawa Hiromi et al. (see attached pdf) (Year: 2008).\*

*Primary Examiner* — Sunita Reddy
(74) *Attorney, Agent, or Firm* — Harness, Dickey & Pierce, P.L.C.

(57) ABSTRACT

A control apparatus includes: an acquisition unit configured to acquire first information from a first sensor, the first information including biological information of a user of a bed, the bed including a back section, and a controller configured to determine a timing when the user is to wake up based on the first information. If the user is to wake up, the controller performs at least one of an operation of increasing lightness at the location of the bed and an operation of sending wind toward the bed after increasing an angle of the back section.

14 Claims, 15 Drawing Sheets

(58) Field of Classification Search
CPC ... A61B 5/6805; A61B 5/6814; A61B 5/6891; G08B 21/22; G08B 19/00; G05B 19/4183; A47C 19/045; A47C 20/04; A47C 21/003; A47C 21/044; A47C 27/081; A47C 27/10; A47C 31/008; A61F 5/56
USPC .................................................. 600/26–28
See application file for complete search history.

(56) References Cited

U.S. PATENT DOCUMENTS

| | | | | |
|---|---|---|---|---|
| 2006/0106275 | A1* | 5/2006 | Raniere | A61M 21/02 600/26 |
| 2006/0123552 | A1* | 6/2006 | Ben-Levi | A61G 7/001 5/81.1 R |
| 2009/0024005 | A1* | 1/2009 | Lewicke | A61B 5/686 600/595 |
| 2011/0224510 | A1* | 9/2011 | Oakhill | A61B 5/4815 600/301 |
| 2012/0085231 | A1* | 4/2012 | Kristensson | F24F 11/80 96/397 |
| 2015/0351982 | A1* | 12/2015 | Krenik | A47C 23/06 5/616 |
| 2016/0015184 | A1* | 1/2016 | Nunn | A47C 27/082 700/282 |
| 2016/0314672 | A1* | 10/2016 | Wiggermann | A61B 5/1117 |
| 2017/0003666 | A1* | 1/2017 | Nunn | G16H 40/63 5/713 |
| 2017/0135883 | A1* | 5/2017 | Franceschetti | G05B 19/042 |
| 2017/0354268 | A1* | 12/2017 | Brosnan | A47C 21/048 |
| 2018/0168485 | A1* | 6/2018 | Chen | A61B 5/4812 |
| 2018/0177975 | A1* | 6/2018 | Goto | A61B 5/4818 |
| 2018/0214091 | A1* | 8/2018 | Baker | A61G 7/018 |
| 2019/0008284 | A1* | 1/2019 | Gehrke | A61G 7/015 |
| 2020/0205580 | A1* | 7/2020 | Sayadi | A61B 5/4806 |
| 2020/0253384 | A1 | 8/2020 | Kubota et al. | |
| 2022/0330892 | A1* | 10/2022 | Lee | A61G 7/0573 |

FOREIGN PATENT DOCUMENTS

| | | |
|---|---|---|
| JP | 2005-334283 A | 12/2005 |
| JP | 2008-010274 A | 1/2008 |
| WO | WO-2017-017784 A1 | 2/2017 |
| WO | WO-2019/176190 A1 | 9/2019 |

* cited by examiner

CONTROL APPARATUS

CROSS-REFERENCE TO RELATED APPLICATION

This patent application is based on and claims priority pursuant to 35 U.S.C. § 119 to Japanese Patent Application No. 2019-188189, filed on Oct. 11, 2019 in the Japanese Patent Office, the entire contents of which is hereby incorporated by reference.

FIELD

Embodiments relate to a control apparatus.

BACKGROUND

For example, there are beds with a variable back angle. Control apparatuses for controlling beds and the like are requested to be able to provide high-quality sleep.

DETAILED DESCRIPTION

Figure 1:
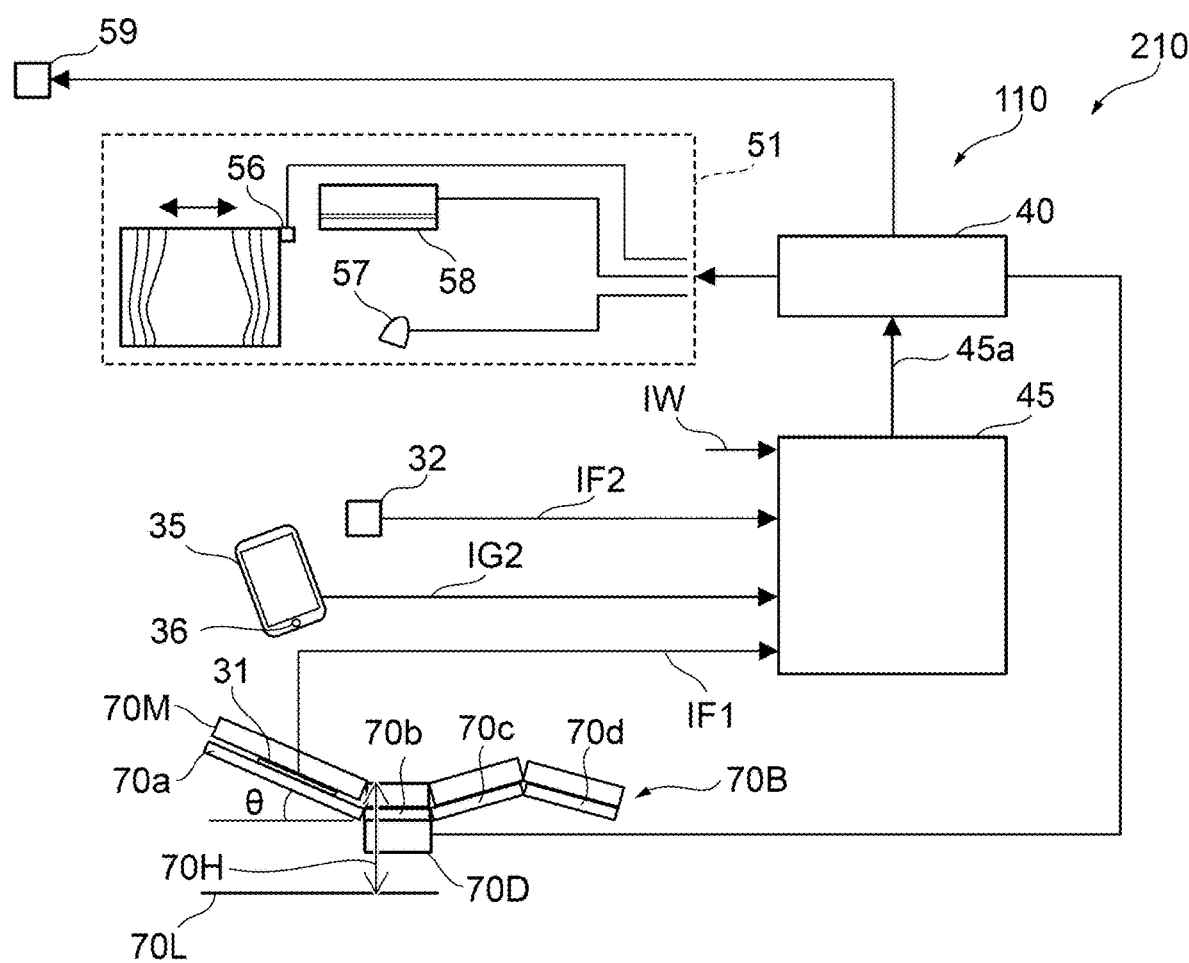
FIG. 1 is a schematic view illustrating a control apparatus according to a first embodiment.

One or more embodiments are now described with reference to the drawings, wherein like reference numerals are used to refer to like elements throughout. In the following description, for purposes of explanation, numerous specific details are set forth in order to provide a thorough understanding of the various embodiments. It is evident, however, that the various embodiments can be practiced without these specific details (and without applying to any particular networked environment or standard).

As used in this disclosure, in some embodiments, the terms "component," "system" and the like are intended to refer to, or comprise, a computer-related entity or an entity related to an operational apparatus with one or more specific functionalities, wherein the entity can be either hardware, or a combination of hardware and software in execution.

One or more components may reside within a process and/or thread of execution and a component may be localized on one computer and/or distributed between two or more computers. In addition, these components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software application or firmware application executed by a processor, wherein the processor can be internal or external to the apparatus and executes at least a part of the software or firmware application. As yet another example, a component can be an apparatus that provides specific functionality through electronic components without mechanical parts, the electronic components can comprise a processor therein to execute software stored on a non-transitory electronic memory or firmware that confers at least in part the functionality of the electronic components. While various components have been illustrated as separate components, it will be appreciated that multiple components can be implemented as a single component, or a single component can be implemented as multiple components, without departing from example embodiments. Further, the various embodiments can be implemented as a method, apparatus or article of manufacture using standard programming and/or engineering techniques to produce software, firmware, hardware or any combination thereof to control a computer to implement the disclosed subject matter. The term "article of manufacture" as used herein is intended to encompass a computer-readable (or machine-readable) device or computer-readable (or machine-readable) storage/communications media having a computer program stored thereon. For example, computer readable storage media can comprise, but are not limited to, magnetic storage device (e.g., hard disk, floppy disk, magnetic strips), optical disks (e.g., compact disk (CD), digital versatile disk (DVD)), smart cards, and flash memory devices (e.g., card, stick, key drive). Of course, those skilled in the art will recognize many modifications can be made to this configuration without departing from the scope or spirit of the various embodiments.

In addition, the words "example" and "exemplary" are used herein to mean serving as an instance or illustration. Any embodiment or design described herein as "example" or "exemplary" is not necessarily to be construed as preferred or advantageous over other embodiments or designs. Rather, use of the word example or exemplary is intended to present concepts in a concrete fashion. As used in this application, the term "or" is intended to mean an inclusive "or" rather than an exclusive "or". That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Embodiments described herein can be exploited in substantially any wireless communication technology, comprising, but not limited to, wireless fidelity (Wi-Fi), global system for mobile communications (GSM), universal mobile telecommunications system (UMTS), worldwide interoperability for microwave access (WiMAX), enhanced general packet radio service (enhanced GPRS), third generation partnership project (3GPP) long term evolution (LTE), third generation partnership project 2 (3GPP2) ultra mobile broadband (UMB), high speed packet access (HSPA), Z-Wave, Zigbee and other 802.XX wireless technologies and/or legacy telecommunication technologies.

In general, one aspect of the present application is a control apparatus including: an acquisition unit that is capable of acquiring first information which is acquired from a first sensor capable of acquiring biological information of a user of a bed on the bed; and a controller that is configured to judge a timing when the user is to wake up based on the first information, in which, when the user is to wake up, the controller performs at least one of an operation of increasing lightness at the location of the bed and an operation of sending wind toward the bed after increasing a back angle of the bed.

Hereinbelow, embodiments are described with reference to the drawings.

The drawings are schematic or conceptual. Throughout the specification of the present application and the drawings, constituents that are the same as those already described in relation to the previously mentioned drawings are given the same reference signs and their detailed description is omitted as needed.

First Embodiment

FIG. 1 is a schematic view illustrating a control apparatus according to a first embodiment.

As illustrated in FIG. 1, a bed system 210 according to the embodiment includes: a bed 70B; and a control apparatus 110.

The control apparatus 110 according to the embodiment includes: an acquisition unit 45; and a controller 40. The acquisition unit 45 is configured to acquire first information IF1. In this example, a first sensor 31 acquires the first information IF1. The first sensor 31 is capable of presuming the posture of a user of the bed 70B at the time when the user is on the bed 70B. For example, the first information IF1 includes the result of presumption on the posture of the user on the side of or on the bed 70B.

The posture of the user on the bed 70B includes a supine position, a lateral position, and a prone position, for example. In the supine position, the face of the user faces upward. In the lateral position, the face of the user faces sideward. In the prone position, the face of the user faces downward (the direction toward a mattress 70M).

For example, the first sensor 31 is placed below the mattress 70M of the bed 70B. The first sensor 31 is capable of detecting the force (e.g. gravity, acceleration, or weight) or vibration (including body motion) of the user, for example. The first sensor 31 may be capable of detecting the body movement of the user, for example. The first sensor 31 may be capable of detecting biological information, such as a breathing rate and a heart rate, of the user. The first sensor 31 may calculate the breathing rate, the heart rate, and the like of the user from the vibration using signal processing such as frequency analysis. For example, the first sensor 31 may include an image device for taking an image of the user. For example, the first sensor 31 may include an acceleration meter that the user wears on his/her forehead or body (including clothes). Any method including an eyeglasses type, a band type, a belt type, an attachment type, a cap type, and an underwear type may be employed as a wearing method. An example of the first sensor 31 is to be described later.

The acquisition unit 45 is an input port, for example. The acquisition unit 45 may be an input/output port, for example. The acquisition unit 45 includes an input circuit and the like, for example. The acquisition unit 45 is configured to acquire the first information IF1 from the first sensor 31 through any of wired and wireless methods.

The controller 40 is capable of receiving an output 45a from the acquisition unit 45. The controller 40 is capable of controlling an environment controller 51 and a drive unit 70D.

The environment controller 51 is capable of controlling at least one of lightness and wind at the location of the bed 70B. The environment controller 51 includes a lighting device 57, for example. The lighting device 57 includes a light emitting element and the like, for example. The environment controller 51 may include a dimmer 56 and the like, for example. The dimmer 56 includes a curtain, a "window shade", or the like, for example. For example, when the dimmer 56 opens, the location of the bed 70B is lightened by external light. For example, when the dimmer 56 closes, the location of the bed 70B is darkened. For example, the environment controller 51 is capable of performing at least one of an operation of irradiating the location of the bed 70B with light and an operation of opening the dimmer 56 located in a room where the bed 70B is placed. The environment controller 51 may include a blower 58. The blower 58 is designed to send wind toward the bed 70B, for example. The blower 58 may be an air conditioner, for example. The environment controller 51 may include a combined device of a light irradiator and a blower.

The drive unit 70D is capable of changing a back angle $\theta$ of the bed 70B. For example, the back angle $\theta$ is the angle of a back region in an upper surface of the bed 70B with respect to a horizontal surface. For example, the back angle $\theta$ is the angle of the back region in the upper surface of the bed 70B with respect to a floor 70L on which the bed 70B is placed, for example.

For example, the back angle $\theta$ may be the angle of the back region with respect to a waist region in the upper surface of the bed 70B. For example, when the bed 70B includes a back section 70a and a seat section 70b, the back angle $\theta$ is the angle of the back section 70a with respect to the seat section 70b. In this case, the drive unit 70D is capable of changing the angle of the back section 70a of the bed 70B. The drive unit 70D includes an actuator and the like, for example. A drive member coupled to the drive unit 70D such as an actuator is connected to the back section. The angle of the back section is changed by the operation of the actuator. Back raising is performed by increasing the angle of the back section. Back lowering is performed by decreasing the angle of the back section.

In the embodiment, the bed 70B may include an air mattress. As is to be described later, the air mattress includes waist air cells and back air cells. The back angle $\theta$ (the angle of the back of the user lying on the air mattress with respect to the waist of the user) can be increased by setting the pressure of the back air cells higher than the pressure of the waist air cells. The back angle $\theta$ is decreased by lowering the pressure of the back air cells. In this manner, when increasing the back angle θ, the drive unit 70D may set the pressure of the back air cells higher than the pressure of the waist air cells.

In the bed 70B, in addition to the change of the angle of the back section, the angle of other portions of the bed 70B (such as an upper leg section 70c and a lower leg section 70d) may be adjustable.

The drive unit 70D may be capable of changing a height 70H of the bed 70B. The height 70H is the height of the upper surface of the bed 70B with respect to the floor 70L.

For example, the controller 40 may be capable of controlling the environment controller 51 and the drive unit 70D through any of wired and wireless methods. The controller 40 may be provided at any location. The controller 40 may be provided at any position in the room where the bed 70B is placed. The controller 40 may be placed outside the room. The controller 40 may be provided inside the bed 70B.

The controller 40 may be provided inside the first sensor 31. At least a part of the function of the controller 40 may be implemented by a control circuit and the like included in the first sensor 31. The controller 40 may be a mobile terminal such as a smartphone.

The controller 40 may acquire second information IF2 from a second sensor 32. For example, the second sensor 32 may be configured to detect lightness at a location (such as the room) where the bed 70B is placed. The second sensor 32 may be configured to detect at least one of temperature and humidity at the location (such as the room) where the bed 70B is placed.

The controller 40 may control a display device 59. The display device 59 is configured to emit light, for example. The display device 59 may be configured to display the status of the user and the like, for example. An example of the operation of the display device 59 is to be described later.

The controller 40 performs an operation to be described later "when the user is to wake up". For example, the first sensor 31 detects the body movement and the like (including the breathing rate, the heart rate, and the like) of the user on the bed 70B. The first sensor 31, the controller 40, or the like is capable of detecting that the user awakes from sleep based on this detection result, or capable of presuming that the user is to wake up based on information on the prescribed time and the like. For example, the timing "when the user is to wake up" is derived based on the result of detecting that the user awakes from sleep, the result of presuming that the user is to wake up, and the like.

For example, the first sensor 31, the controller 40, or the like detects at least one of events that "the body motion increases", that "the heart rate increases", and that "the breathing rate increases" around the preset time (e.g. wake-up time). The first sensor 31 or the controller 40 determines whether a timing one of the events has occurred is around the preset time based on a cycle of a REM state and a non-REM state of the user for example. The controller 40 will estimate whether the user is the REM state or the non-REM state in accordance with the change of the body motion, the heart rate, or the breathing rate. The first sensor 31 or the controller 40 may determine that a timing one of the events has occurred is around the preset time if one of the events has occurred predetermined time (e.g. 1 hour) before the preset time.

Based on this detection result, the first sensor 31, the controller 40, or the like can presume that the user transitions to the condition of being expected to awake from sleep and that the user awake from the condition of being expected to awake. For example, the first sensor 31, the controller 40, or the like can detect that the user is "expected to awake" when the body motion, the heart rate, the breathing rate, or the like exceeds a first threshold. The condition of being expected to awake indicates a condition that the user has not awoke yet but is likely to awake. In addition, the first sensor 31, the controller 40, or the like can detect that the user is "awake" when the body motion, the heart rate, the breathing rate, or the like exceeds a second threshold which is greater than the first threshold.

The first sensor 31, the controller 40, or the like judges that the user is to wake up by detecting that the user is in the condition of being expected to awake. The embodiment is not limited to this case, and the first sensor 31, the controller 40, or the like may judge that the user is to wake up by detecting that the user is awake.

Hereinbelow, an example of the operation performed "when the user is to wake up" is described.

When the user is to wake up, the control apparatus or the bed system of this embodiment increases the back angle of the bed 70B first, and then performs control to send wind or emit light toward the bed 70B after the back of the bed is raised. Specific control methods corresponding to sleeping postures of the user are to be described in detail below.

Figure 2:
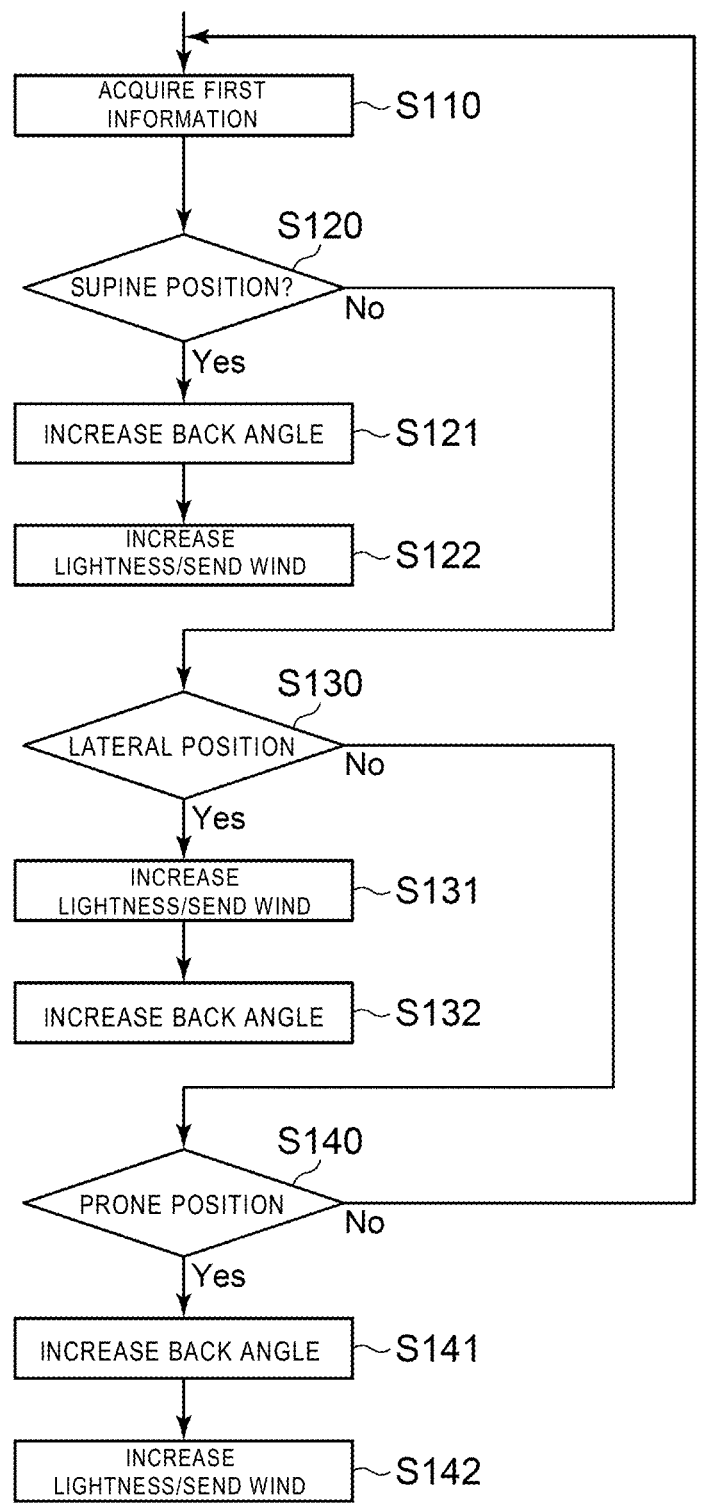
FIG. 2 is a flowchart illustrating an operation of the control apparatus according to the first embodiment.

FIG. 2 is a flowchart illustrating an operation of the control apparatus according to the first embodiment.

As illustrated in FIG. 2, the acquisition unit 45 acquires the first information IF1 from the first sensor 31 (Step S110).

As illustrated in FIG. 2, the controller 40 judges whether or not the first information IF1 acquired from the first sensor 31 when the user is to wake up corresponds to the case where the user is in the supine position (Step S120). If the first information IF1 corresponds to the case where the user is in the supine position, the controller 40 increases the back angle θ (Step S121). The increased back angle θ is greater than 0 degree and 70 degrees or smaller, for example. The back angle θ before the increase is 0 degree or greater and smaller than 70 degrees, for example. The increased back angle θ may be greater than 0 degree and 30 degrees or smaller, for example.

After Step S121, the controller 40 performs at least one of an operation of increasing lightness at the location of the bed 70B and an operation of sending wind toward the bed 70B (Step S122). For example, when increasing lightness at the location of the bed 70B, the controller 40 causes the environment controller 51 to control at least one of the lighting device 57 and the dimmer 56 to increase lightness. For example, when sending wind toward the bed 70B, the controller 40 controls the blower 58 to send wind toward the bed 70B.

For example, the system may have such a configuration as to store the set position and orientation of the bed 70B and emit light or send wind toward the position and orientation. For example, the system may have such a configuration as to detect the position of the bed 70B or the position of the head of the user on the bed 70B with a camera or the like and emit light or send wind toward the position thus detected. For example, the system may have such a configuration as to emit light or send wind toward the position of an RFID (radio frequency identifier) provided in a pillow. For example, the system may have such a configuration as to emit light or send wind toward a position lower than the head-side end of the back section 70a of the bed 70B by about one-third of the height. Wind or light may be output from a bed board.

The user wakes up by performing at least one of increasing lightness and sending wind. In the embodiment, the user can reliably wake up by performing at least one of increasing lightness and sending wind after increasing the back angle θ when the user is to wake up and is in the supine position.

For example, when the user is to wake up, by performing at least one of increasing lightness and sending wind after increasing the back angle θ, the user can wake up more reliably than in the case of increasing the back angle θ only and performing neither of increasing lightness and sending wind.

For example, even in the case of increasing lightness and sending wind when the user is to wake up while the bed surface is flat without increase of the back angle θ, the user turns his/her head away from light or wind, so that the user is less likely to wake up.

In the embodiment, the user can wake up reliably by performing at least one of increasing lightness and sending wind after increasing the back angle θ when the user is in the supine position.

According to the embodiment, it is possible to provide the control apparatus and the bed system which enable the user to wake up reliably. According to the embodiment, it is possible to provide the control apparatus and the bed system which are capable of providing high quality sleep.

In general, there is a reference example of controlling the room at an appropriate temperature or lightness when the user wakes up. In this reference example, no wind or light is fed toward an intended position (the position of the user on the bed 70B). In this embodiment, wind or light may be fed in every direction instead of being fed toward the position of the user on the bed 70B after the user wakes up as a result of Step S122, for example.

As illustrated in FIG. 2, the process proceeds to Step S130 below if the first information IF1 does not correspond to the case where the user is in the supine position in Step S120 above, for example.

In Step S130, the controller 40 judges whether or not the first information IF1 acquired from the first sensor 31 when the user is to wake up corresponds to the case where the user is in the lateral position. If the first information IF1 corresponds to the case where the user is in the lateral position, the controller 40 performs at least one of an operation of increasing lightness at the location of the bed 70B and an operation of sending wind toward the bed 70B (Step S131). The user is apt to change his/her posture from the lateral position in order to avoid light or wind. For example, the user changes his/her posture from the lateral position to the supine position. By performing at least one of the operation of increasing lightness at the location of the bed 70B and the operation of sending wind toward the bed 70B, this operation guides the user to change his/her posture to the supine position.

More specifically, assume that the user is lying on the bed 70B in a left lateral position, for example. At this time, in order to send wind or emit light onto the face of the user, the controller 40 performs the operation of increasing lightness or the operation of sending wind so that wind or light is fed to the position of the user from the left side. When the face of the user moves from the left lateral position to the supine position, the controller changes the direction of wind or light so that it follows the movement of the face of the user.

After Step S131, when the user changes his/her posture to the supine position, the controller 40 increases the back angle θ (Step S132). By performing the operation of the above order when the user is in the lateral position, the user can wake up more reliably.

For example, if the controller increases the back angle θ when the user is in the lateral position without increasing lightness or sending wind, the user's body bends laterally and thus the user feels a sense of discomfort. For example, by setting the back angle θ at 10 degrees or smaller, it is possible to let the user feel a sense of discomfort to a moderate degree while preventing the user from getting injured or feeling an excessive sense of discomfort. This sense of discomfort causes the user to change his/her posture from the lateral position to the supine position, for example. By further increasing the back angle θ after Step S131 (Step S132) and then performing at least one of increasing lightness and sending wind, the user having been in the lateral position in the first place can wake up more reliably.

As illustrated in FIG. 2, the process proceeds to Step S140 below if the first information IF1 does not correspond to the case where the user is in the lateral position in Step S130 above, for example.

In Step S140, the controller 40 judges whether or not the first information IF1 acquired when the user is to wake up corresponds to the case where the user is in the prone position.

If the first information IF1 corresponds to the case where the user is in the prone position, the controller 40 increases the back angle θ (Step S141). Here, the back angle θ observed after the back angle is increased when the user is in the prone position is smaller than the back angle θ observed after the back angle is increased when the user is in the supine position. The back angle θ observed after the back angle is increased when the user is in the prone position is greater than 0 degree and 10 degrees or smaller, for example.

If the back angle θ is increased excessively when the user is in the prone position, the user feels a sense of discomfort. For example, the user's body might be damaged. By increasing the back angle θ by a small angle when the user is in the prone position, this inhibits the user from feeling an excessive sense of discomfort. At the same time, by performing at least one of increasing lightness and sending wind after guiding the user to change his/her posture to the supine position, the user can wake up more reliably.

As illustrated in FIG. 2, if the first information IF1 corresponds to the case where the user is in the prone position in Step S140, the controller 40 may perform at least one of an operation of increasing lightness at the location of the bed 70B and an operation of sending wind toward the bed 70B (Step S142). The order of Step S141 and Step S142 may be swapped for each other.

After Step S122, S132, or S142 is over, the process returns to Step S110 and iterates until the user wakes up.

In the embodiment, the user feels stimulated to awake by increasing lightness at the location of the bed 70B and sending wind toward the bed 70B, for example. By performing these operations and control over the back angle θ in combination, this allows the user to wake up more reliably. According to the embodiment, it is possible to provide the control apparatus and the bed system which are capable of providing high quality sleep in terms of providing the user with a sense of security that the user can wake up reliably.

The acquisition unit 45 may further acquire information on lightness at the location of the bed 70B. The information on lightness at the location of the bed 70B may be included in the second information IF2 (see FIG. 1) acquired from the second sensor 32, for example.

Lightness at the location of the bed 70B might be light enough already when the user is to wake up. In this case, the user is more likely to face a direction to avoid light and is less likely to be in the supine position. The controller 40 may perform the following operation. If lightness at the location of the bed 70B is a threshold or greater when the user is to wake up, even if the first information IF1 indicates that the user is in the supine position, the controller 40 increases the back angle θ based on judgment that the user is more likely to be in the lateral position or the prone position (Step S141). In this case, since lightness is the threshold or greater, Step S142 may be omitted. Alternatively, the controller sends wind in Step S142. The back angle θ observed after the back angle is increased in this case is also smaller than the back angle θ observed after the back angle is increased when the user is in the supine position. The back angle θ observed after the back angle is increased when the user is in the prone position is greater than 0 degree and 10 degrees or smaller.

If lightness at the location of the bed 70B is smaller than the threshold when the user is to wake up, the controller 40 may increase lightness at the location of the bed 70B, and then increase the back angle θ after making sure that the user is in the lateral position or the prone position.

In this manner, in the embodiment, the operation of the controller 40 may vary depending on whether or not lightness at the location of the bed 70B observed when the user is to wake up is the threshold or greater.

In the embodiment, the first sensor 31 may presume whether the user is sleeping or awakes. For example, the first sensor 31 detects the body movement and the like (including the breathing rate, the heart rate, and the like) of the user. For example, the first sensor presumes that the user is sleeping if the body movement is small. For example, the first sensor presumes that the user awakes if the body movement is large. The controller 40 may control the display mode of the display device 59 (see FIG. 1) so that it corresponds to the condition that the user is sleeping or that the user awakes thus presumed. For example, the controller changes the color of light emitted from the display device 59 so that it corresponds to the condition that the user is sleeping or that the user awakes.

For example, the display device 59 emits blue light when the user is sleeping. The display device 59 emits yellow light when the user is awake or the user gets up. The display device 59 emits white light when the user is away from the bed 70B. Alternatively, the display device 59 may turn on the light or turn off the light in specific conditions, e.g. turn on the light only when the user is sleeping.

The display device 59 may be placed in the location (room) where the bed 70B is placed, or alternatively may be provided at other locations (such as other rooms or corridor).

For example, the bed system 210 controls the display device 59 so that the display device takes any of first and second modes. In the first mode, the display device 59 emits blue light, yellow light, or white light. In the second mode, the display device 59 emits light other than blue light, yellow light, and white light (e.g. orange light). For example, in the second mode, the display device 59 does not change the color of light depending on the condition of the user and is used as a normal lighting device. The bed system 210 may switch the display device 59 between the first mode and the second mode in such a way that the display device is set at the first mode from 10 p.m. to 6 a.m. and is set at the second mode in a period other than this period. The bed system 210 may switch the display device 59 between the first mode and the second mode with time. This switching may be capable of being made through a screen of an electronic device 35. The switching may be made by a physical switch.

When the bed system 210 according to the embodiment is implemented in a nursing care facility, hospital, or the like, the display device 59 may be provided in a corridor outside a room. In this case, the display device 59 functions as an indicator for indicating the condition of the user in each room.

For example, the display device 59 is provided at a location different from the location where the bed 70B is placed. For example, a family member of the user of the bed 70B and the like can recognize the condition of the user at a location away from the bed 70B. This makes it possible to provide more convenient control apparatus and bed system.

According to the first embodiment, it is possible to provide the control apparatus and the bed system which are capable of providing high quality sleep.

Second Embodiment

In a second embodiment, the control apparatus 110 also includes the acquisition unit 45 and the controller 40 (see the relevant drawing). The acquisition unit 45 is configured to acquire the first information IF1 and the second information IF2 (see FIG. 1). The first information IF1 is acquired by the first sensor 31 that is configured to detect the condition of the user of the bed 70B. The second information IF2 includes a detection value of at least one of temperature and humidity around the bed 70B. The second information IF2 may be acquired by the second sensor 32 (see FIG. 1), for example. The second information IF2 may be acquired by the controller 40, for example. The controller 40 is configured to control the drive unit 70D that is capable of changing the back angle θ of the bed 70B.

Hereinbelow, an example of the operation of the controller 40 in the second embodiment is described. The following operation of the controller 40 is executed in a "falling asleep mode". For example, when an input is made to the bed 70B from the user or the like or when a predetermined time arrives, the bed 70B transitions to the "falling asleep mode". In The "falling asleep mode", the bed 70B is operated automatically. For example, the back angle θ and the like is controlled automatically.

Figure 3A:
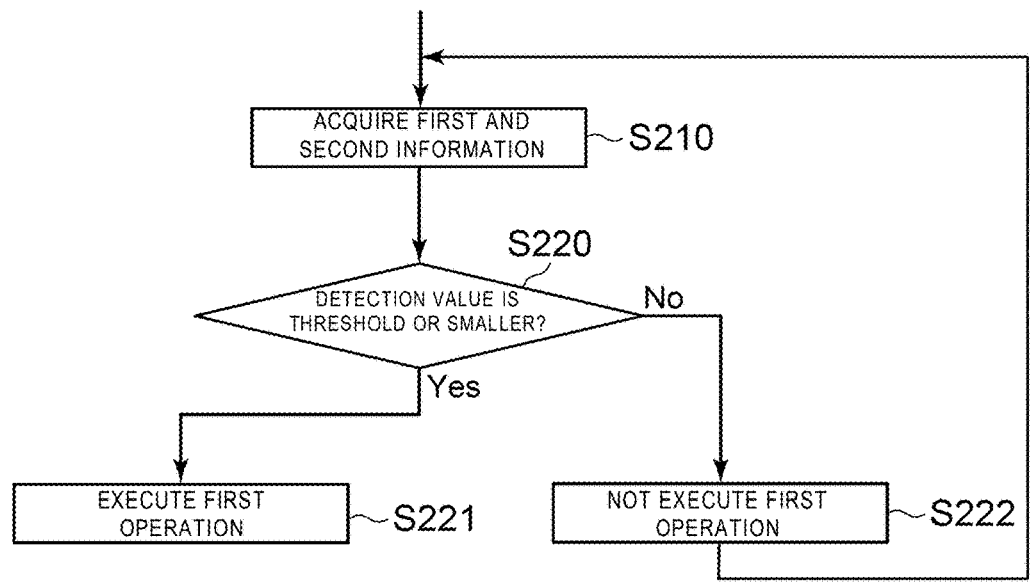
FIGS. 3A and 3B are flowcharts illustrating an operation of a control apparatus according to a second embodiment.
Figure 3B:
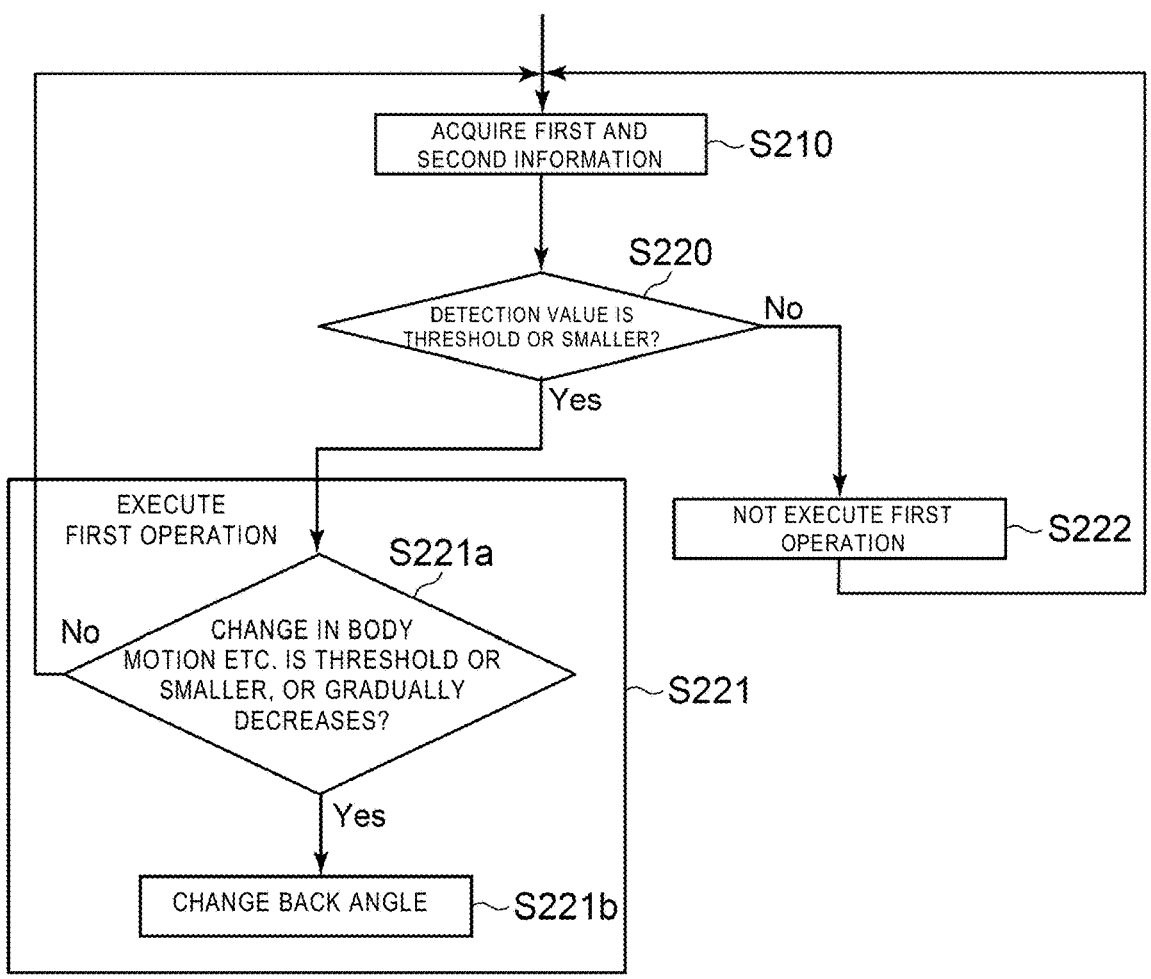

FIG. 3A and FIG. 3B are flowcharts illustrating the operation of the control apparatus according to the second embodiment.

As illustrated in FIG. 3A, the acquisition unit 45 acquires the first information IF1 and the second information IF2 (Step S210).

The controller 40 judges whether or not the detection value of at least one of temperature, humidity, and sound around the bed 70B included in the second information IF2 is a threshold or greater (Step S220). Sound is noise, for example. The controller judges whether or not an awakening probability (e.g. temperature-humidity index) obtained from the temperature and humidity is the threshold or greater. For example, the controller judges whether or not an awakening probability obtained by adding a noise level to the awakening probability obtained from the temperature and humidity is the threshold or greater.

In Step S220, the controller 40 causes the drive unit 70D to execute a first operation if the detection value is the threshold or smaller (Step S221). For example, the threshold is an upper limit of temperature, humidity, or sound at which the user finds it easy to sleep. The user of the bed 70B finds it easy to sleep when the detection value of at least one of the temperature, humidity, and sound around the bed 70B is the threshold or smaller.

The process may return to Step S210 after Step S221.

In the first operation, the drive unit 70D changes the back angle θ according to the condition of the user of the bed 70B acquired from the first sensor 31.

For example, the first sensor 31 detects the condition of the user. The user is in a sleeping condition under a condition where the body motion acquired from the first sensor 31 is small (the condition judged as sleeping). The user is in an awakening condition under a condition where the body motion acquired from the first sensor 31 is large (the condition judged as awakening). For example, in the above first operation, if the body motion acquired from the first sensor 31 is small, the drive unit decreases the back angle θ. This facilitates the user rolling over without interrupting the sleep of the user. For example, in the above first operation of the falling asleep mode, if the condition obtained by the first sensor 31 indicates that the user is awake for a predetermined period or longer, the drive unit may increase the back angle θ. This facilitates the user falling asleep.

For example, the first operation includes an operation of decreasing the back angle θ when a signal value included in the first information IF1 (such as the amount of body motion, the breathing rate, or the heart rate) decreases with time or when the value varies by a threshold or smaller. For example, the first operation includes an operation of decreasing the back angle θ when the user is in a falling asleep condition (when the body motion is small).

In Step S220 of FIG. 3A, the controller 40 does not cause the drive unit 70D to execute the first operation when the detection value exceeds the threshold (Step S222). The process returns to Step S210 after Step S222. The user is likely to wake up when the detection value of at least one of the temperature, humidity, and sound around the bed 70B exceeds the threshold. In this case, if the back angle θ is changed, this might hamper the user's sleep. By not executing the first operation to change the back angle θ when the detection value exceeds the threshold i.e. when the user's sleep is likely to be interrupted, this inhibits the user's sleep from being interrupted.

By executing the above first operation to change the back angle θ when the detection value of at least one of the temperature, humidity, and sound around the bed 70B is the threshold or smaller, it is possible to provide the user with sleep less likely to be interrupted.

The threshold regarding the temperature is 28 degrees, for example. The threshold regarding the humidity is 80 percent, for example. The threshold regarding the temperature may be changed according to the humidity. The threshold regarding the humidity may be changed according to the temperature. The threshold may be changed to the temperature-humidity index obtained from the temperature and humidity. The threshold may be changed to the awakening probability obtained from the temperature, humidity, and noise level.

For example, the threshold may be adjustable or settable according to the user. For example, the threshold is customizable according to the user. For example, the threshold suitable for the user may be employed based on data on the relationship between the body motion or the like of this user at the time when the user is on the bed 70B and the temperature or humidity. For example, when the body motion of the user is smaller than a certain threshold, this is judged as the temperature/humidity suitable for the user and set as the threshold suitable for the user.

According to the second embodiment, it is possible to provide the control apparatus and the bed system which are capable of providing high quality sleep.

As illustrated in FIG. 3B, in the first operation (Step S221) executed when the detection value exceeds the threshold in Step S220, the controller may judge whether or not a temporal change in the signal value (including the body motion) included in the first information IF1 is the threshold or smaller, or whether or not the value gradually decreases (Step S221a), and change (e.g. decrease) the back angle θ if the temporal change in the signal value (including the body motion) included in the first information IF1 is the threshold or smaller, or if the value gradually turns smaller (Step S221b). By changing the back angle θ if the temporal change in the body motion is the threshold or smaller, it is possible to inhibit the user's sleep from being interrupted. If the temporal change in the body motion exceeds the threshold, the process returns to Step S210. For example, the controller compares the signal values included in the first information IF1 in two periods (a first period and a second period that comes after the first period), and decreases the back angle by a preset angle if the signal value in the second period is smaller than the signal value in the first period or if the value varies by the threshold or smaller (Step S221b). Then, the controller may iterate this operation and gradually decrease the back angle so that the angle reaches a desired angle.

The process may return to Step S210 after Step S221b.

Third Embodiment

In a third embodiment, the control apparatus 110 includes the acquisition unit 45 and the controller 40 (see FIG. 1). The acquisition unit 45 is configured to acquire the first information IF1 and second information IG2. The first information IF1 is acquired by the first sensor 31 that is configured to detect the condition of the user of the bed 70B. The second information IG2 is acquired by the electronic device 35 that is manipulated by the user. The electronic device 35 may be a smartphone, for example. The electronic device 35 may be a computer, for example. At least apart of the operation of the controller 40 may be implemented by the electronic device 35. The controller 40 is capable of changing the back angle θ of the bed 70B.

Hereinbelow, an example of the operation of the controller 40 in the third embodiment is described. The following operation of the controller 40 is implemented in the "falling asleep mode".

Figure 4:
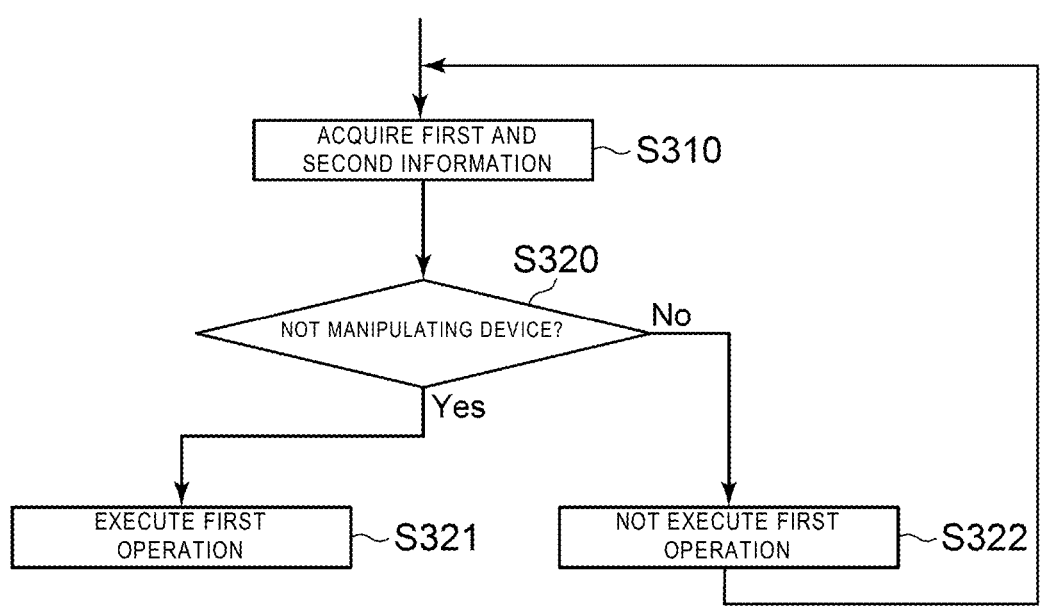
FIG. 4 is a flowchart illustrating an operation of a control apparatus according to a third embodiment.

FIG. 4 is a flowchart illustrating an operation of the control apparatus according to the third embodiment.

As illustrated in FIG. 4, the acquisition unit 45 acquires the first information IF1 and the second information IF2 (Step S310).

As illustrated in FIG. 4, the electronic device 35 judges whether or not the user of the bed 70B is manipulating the electronic device 35 (Step S320). The electronic device 35 includes an acceleration sensor and the like. An acceleration occurs in the electronic device 35 when the user manipulates the electronic device 35. The acceleration is detected by the acceleration sensor, whereby the electronic device 35 can judge whether or not the electronic device is being used. The electronic device 35 may include an input reception device such as a touch panel display. The electronic device 35 can judge whether or not the electronic device is being used based on whether or not an input is made to the input reception device, a period for which the input is made, and the like.

As illustrated in FIG. 4, if the user is not manipulating the electronic device 35 in Step S320, the controller 40 causes the drive unit 70D to execute the first operation (Step S321). In the first operation, the drive unit 70D is controlled by the controller 40 so that it executes the first operation of changing the back angle θ according to the condition of the user.

The process may return to Step S310 after Step S321.

As has been described, in the first operation, the drive unit decreases the back angle θ when the body motion acquired from the first sensor 31 is small (the condition is judged as sleeping). This facilitates the user rolling over. For example, in the first operation, the drive unit increases the back angle θ when the user is manipulating the electronic device 35. This facilitates the user falling asleep again or waking up.

As illustrated in FIG. 4, if the user is manipulating the electronic device 35 in Step S320, the controller 40 does not cause the drive unit 70D to execute the first operation (Step S322). The process returns to Step S310 after Step S322.

In Step S320, when the user is manipulating the electronic device 35, the user might be awake even if the body movement (including the breathing rate, the heart rate, and the like) of the user is small. However, if a judgment is made only based on the first information IF1 from the first sensor 31, the user might be erroneously judged as sleeping. In the embodiment, by not executing the above first operation when the user is manipulating the electronic device 35, it is possible to prevent the first operation from being executed erroneously, whereby the operation at the time of falling asleep including the first operation is executed more properly. In the embodiment, the second information IF2 which is acquired from the electronic device 35 manipulated by the user is prioritized over the first information IF1 which is acquired from the first sensor 31 that detects the condition of the user of the bed and which is a basis of the first operation.

As has been described, the first operation includes the operation of decreasing the back angle θ when the signal value included in the first information IF1 (such as the body motion, the breathing rate, or the heart rate) decreases with time or when the value varies by the threshold or smaller, for example. For example, the first operation includes an operation of increasing the back angle when the user is manipulating the electronic device 35.

According to the third embodiment, it is possible to provide the control apparatus and the bed system which are capable of providing high quality sleep that is suited to the condition of the user judged more accurately.

Since the user might be awake even if a variation in the body movement (including the breathing rate, the heart rate, and the like) of the user is small, in addition to the case where the user is manipulating the electronic device as described above, the user might be watching videos and the like with the electronic device 35. In this case, the user does not manipulate the electronic device 35 but is awake, and therefore moving the bed automatically without intention of the user is sometimes not preferable. Accordingly, in such a case, Step S320 is replaced with a step of judging whether or not the user is watching videos and the like. The process executes the first operation (Step S321) if the user is not watching videos and the like (Step S320, Yes), and does not execute the first operation (Step S322) if the user is watching videos and the like (Step S320, No).

Fourth Embodiment

In a fourth embodiment, the control apparatus 110 includes the acquisition unit 45 and the controller 40 (see FIG. 1). The acquisition unit 45 is capable of acquiring an alarm IW. The alarm IW includes at least one of a first alarm informing of at least one of an intrusion of a person and a fire and a second alarm informing of a disaster. For example, the disaster includes earthquakes, large-scale fires, tsunamis, floods, tornadoes, or the like. The second alarm includes evacuation alarms. Such alarms can be acquired through information networks (including a smartphone and the like) provided in a house (including a facility and the like) where the bed 70B is provided.

The controller 70D is configured to control the drive unit 70D. The drive unit 70D is capable of changing at least one of the back angle θ of the bed 70B and the height 70H of the bed 70B.

Hereinbelow, an example of the operation of the controller 40 in the fourth embodiment is described.

Figure 5:
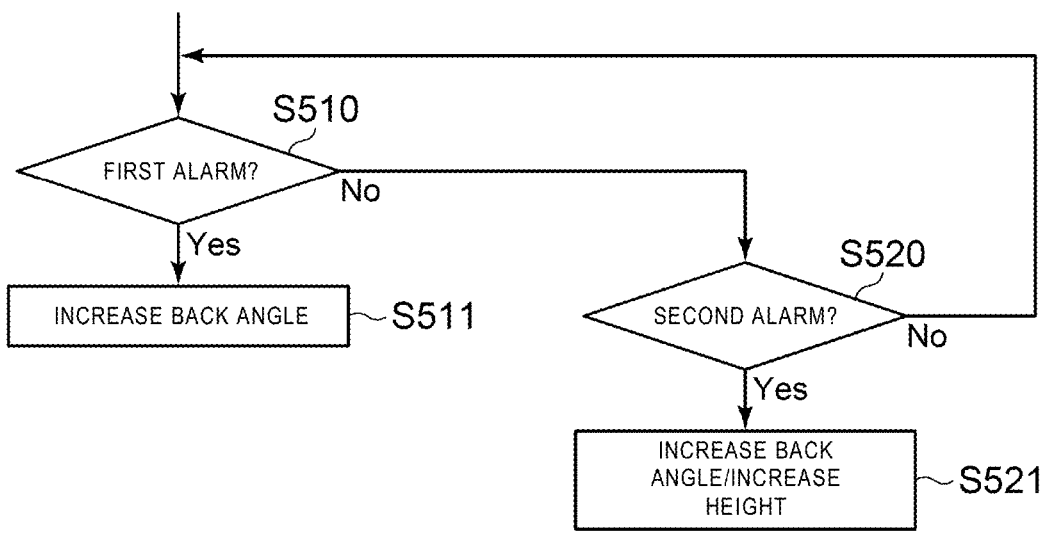
FIG. 5 is a flowchart illustrating an operation of a control apparatus according to a fourth embodiment.

FIG. 5 is a flowchart illustrating an operation of the control apparatus according to the fourth embodiment.

As illustrated in FIG. 5, the controller 40 judges whether or not the acquisition unit 45 has acquired the first alarm, for example (Step S510).

In Step S510, the controller causes the drive unit 70D to increase the back angle θ if the acquisition unit 45 has acquired the first alarm (Step S511). If the first alarm informing of at least one of an intrusion of a person and a fire occurs, an increase of the back angle θ can awake the user reliably. The process may return to Step S510 after Step S511.

In Step S510, the controller 40 judges whether or not the acquisition unit 45 has acquired the second alarm if the acquisition unit 45 has not acquired the first alarm (Step S520).

In Step S520, if the acquisition unit 45 has acquired the second alarm, the controller 40 causes the drive unit 70D to increase the back angle θ and increase the height 70H of the bed 70B (Step S521). By increasing the back angle θ, the user can awake easily. For example, by increasing the height 70H of the bed 70B, the user can slip into the gap between the bed 70B and the floor 70L, which makes it easier to secure the safety of the user in case of a disaster such as an earthquake. The process may return to Step S510 after Step S521.

The process returns to Step S510 if the acquisition unit 45 has not acquired the second alarm in Step S520.

In the embodiment, by increasing the back angle θ when the acquisition unit 45 has acquired the first alarm (an intrusion of a person or a fire), the user can awake easily and thus can easily deal with such an intrusion of a person or a fire. The user can secure his/her safety when the acquisition unit 45 has acquired the second alarm (a disaster).

For example, the back angle θ in the case where the acquisition unit 45 has acquired the second alarm (a disaster) may be larger than the back angle θ in the case where the acquisition unit 45 has acquired the first alarm (an intrusion of a person or a fire). For example, when an emergency evacuation alert informing of a tsunami, break in a levee, a tornado, or the like is issued, by increasing the back angle θ due to reasons such as: some sort of physical reasons e.g. a smartphone is buried under bedding; bodily reasons e.g. hard of hearing; environmental reasons e.g. the user is sleeping with earplugs or while listening to music with earphones, the user can awake easily and secure time to evacuate.

According to the embodiment, since the bed 70B can execute the operation suited to the situation such as an intrusion of a person, a fire, or a disaster, the user can sleep safely. According to the embodiment, it is possible to provide the control apparatus and the bed system which are capable of providing safety.

Step S510 and Step S520 may be executed at the same time or executed in a reverse order.

Fifth Embodiment

In a fifth embodiment, the control apparatus 110 includes the acquisition unit 45 and the controller 40 (see FIG. 1). The acquisition unit 45 is capable of acquiring a sound detection result from a sound device 36. The sound device 36 is a microphone, for example. The sound device 36 may be included in the electronic device 35, for example. The controller 40 is capable of controlling the drive unit 70D that is capable of changing the back angle θ of the bed 70B.

In the embodiment, the controller 40 causes the drive unit 70D to execute an operation of changing the back angle θ when the sound detection result acquired from the sound device 36 includes a snoring sound. For example, by using a smartphone as the electronic device 35 that includes the sound device 36, it is also possible to cause the electronic device 35 to issue an operation command to change the back angle θ to the drive unit 70D. As the result of the command, the back angle θ will increase by the drive unit 70D. If the sound detection result acquired from the sound device 36 includes a snoring sound after increasing the back angle θ (e.g. an angle θ1), the controller 40 causes the drive unit 70D to execute the operation to further raise the back section so that the back angle θ changes from the angle θ1 to an angle θ2. The angle θ2 is larger than the angle θ1. The controller may continue the back raising operation until stopping the snoring sound. After stopping snoring sound, the controller may cause the drive unit 70D to gradually execute a back lowing operation.

By changing the back angle, it is possible to suppress a snoring of the user. According to the embodiment, it is possible to provide the control apparatus and the bed system which are capable of providing high quality sleep not only to the user himself/herself but also to people around the user. The sound device 36 may generate a sound in addition to the detection of sound. The sound device 36 may have a speaker function, for example.

Sixth Embodiment

A sixth embodiment relates to the bed system 210 (see FIG. 1). The bed system 210 includes the control apparatus according to the first to fifth embodiments described above and the bed 70. According to the sixth embodiment, it is possible to provide the bed system which is capable of providing high quality sleep.

Hereinbelow, an example of the bed 70B applied with the embodiment is described.

Figure 6:
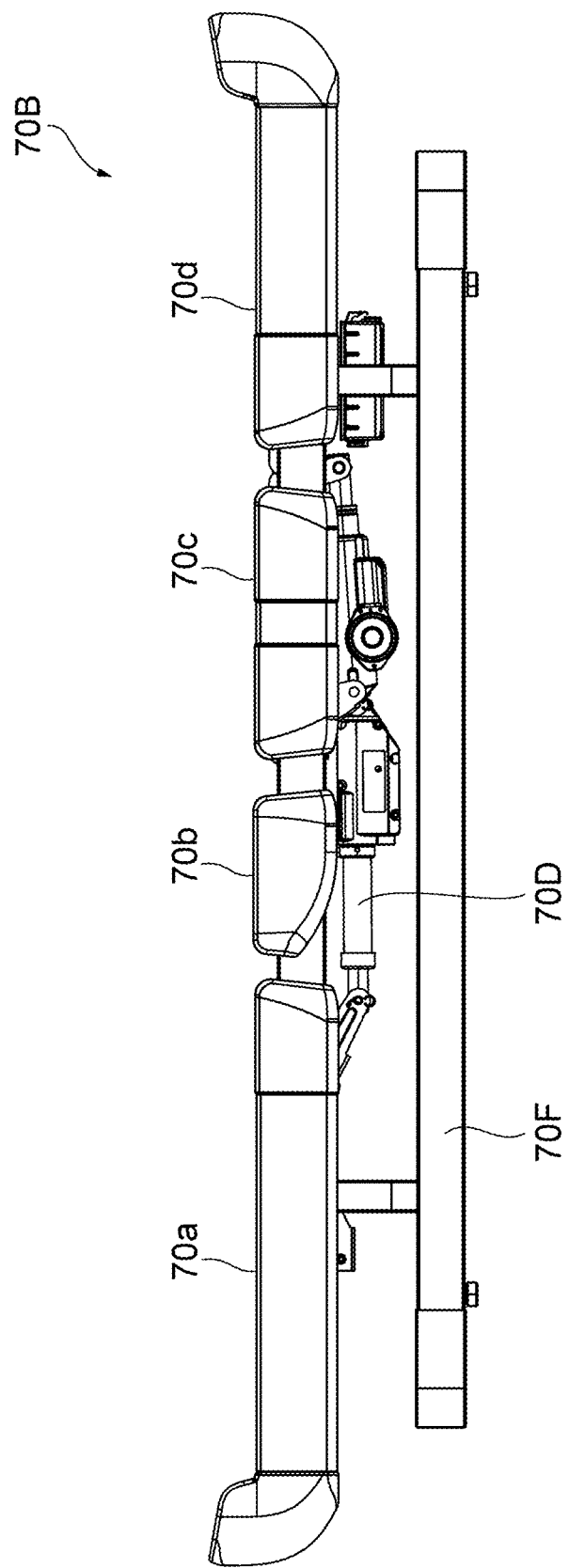
FIG. 6 is a schematic side view illustrating a bed according to the embodiment.

FIG. 6 is a schematic side view illustrating the bed according to the embodiment.

Figure 7:
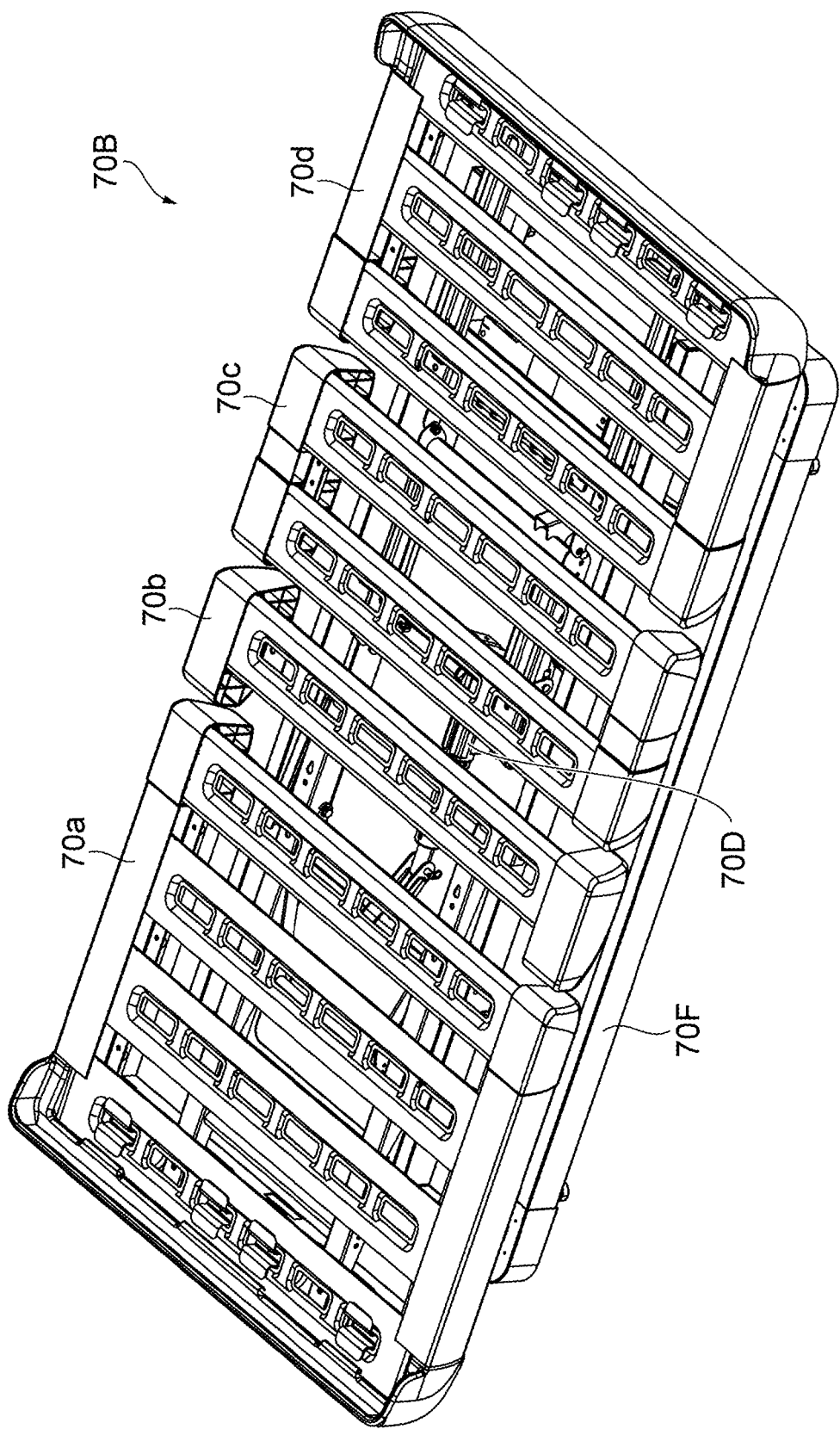
FIG. 7 is a schematic perspective view illustrating the bed according to the embodiment.

FIG. 7 is a schematic perspective view illustrating the bed according to the embodiment.

As illustrated in FIG. 6 and FIG. 7, the bed 70B according to the embodiment includes the back section 70a, the seat section 70b, the upper leg section 70c, the lower leg section 70d, and the like. The back section 70a, the seat section 70b, the upper leg section 70c, and the lower leg section 70d are arranged on a frame 70F. For example, the drive unit 70D is provided between the seat section 70b and the frame 70F. The angles of the back section 70a, the upper leg section 70c, and the lower leg section 70d can be changed by an operation of the drive unit 70D. These angles are angles with respect to the frame 70F.

Hereinbelow, an example of an air mattress applied with the embodiment is described. For example, the shape of the mattress is changed based on a biological signal (first information IF1).

Figure 8:
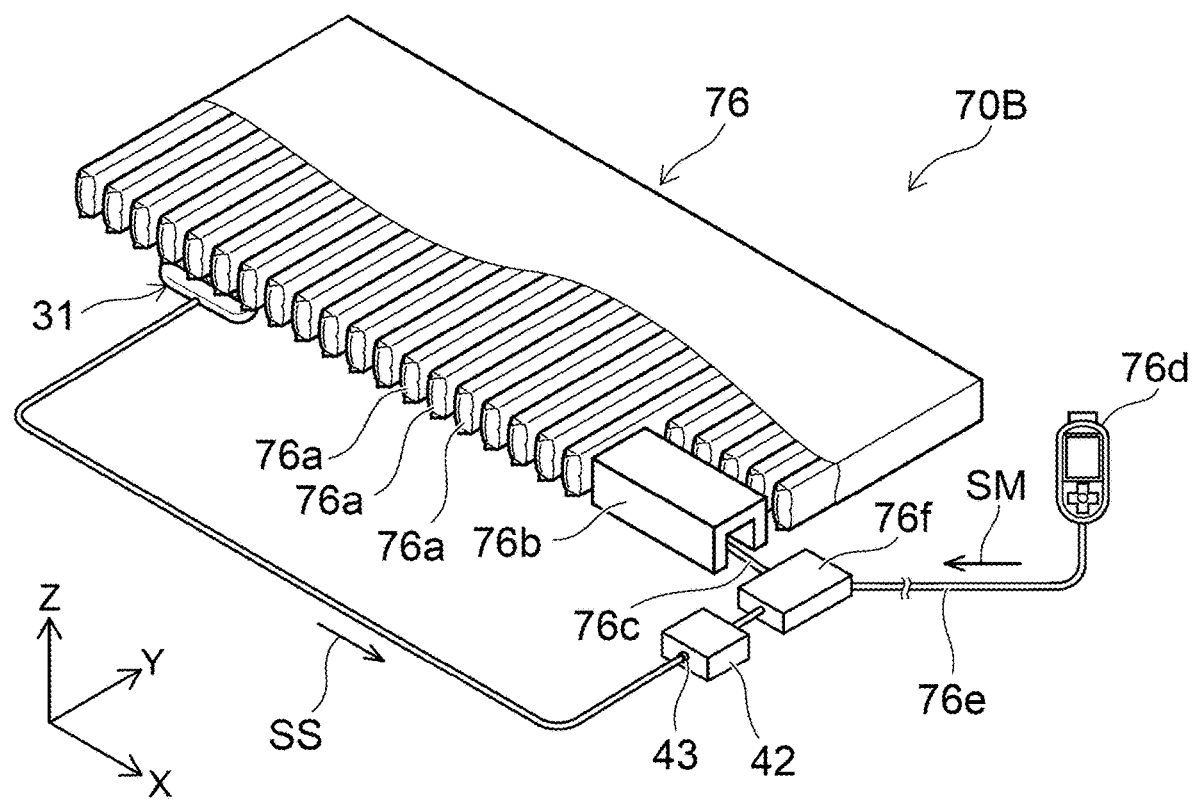
FIG. 8 is a schematic perspective view illustrating a mattress according to the embodiment.

FIG. 8 is a schematic perspective view illustrating the mattress according to the embodiment.

As illustrated in FIG. 8, the bed 70B according to this embodiment includes a mattress 76 and a mattress controller 42. The bed 70B may be further provided with a mattress acquisition unit 43. The mattress acquisition unit 43 may be included in the mattress controller 42. The mattress 76 may be placed on the sections of the bed 70B.

For example, the mattress 76 includes multiple air cells 76a. For example, the multiple air cells 76a are arranged in a direction that connects a head part and a foot part of the mattress 76 (e.g. the X-axis direction). For example, each of the multiple air cells 76a extends in a lateral direction of the mattress 76 (e.g. the Y-axis direction). For example, a pump unit 76b controls the volume of air inside each of the multiple air cells 76a, which changes the pressure inside each of the multiple air cells 76a. For example, this can change the height of each of the multiple air cells 76a (e.g. the position of the upper end of each of the multiple air cells in a Z-axis direction).

For example, a mattress drive unit 76f (e.g. an electric circuit unit) is provided. The pump unit 76b is connected to the mattress drive unit 76f through a cable 76c. The pump unit 76b is operated by a controller of the mattress drive unit 76f, whereby the state of each of the multiple air cells 76a can be controlled separately.

In this example, a mattress manipulation unit 76d is provided. The mattress manipulation unit 76d is connected to the mattress drive unit 76f through a cable 76e. The mattress manipulation unit 76d is configured to receive manipulation by the user of the mattress 76, for example. A signal SM associated with the manipulation received by the mattress manipulation unit 76d is fed to the mattress drive unit 76f, whereby the state of the mattress 76 (such as the shape of each of the multiple air cells 76a) can be controlled manually.

In the embodiment, in addition to the manual control, the state of the mattress 76 (such as the shape) is controlled under automatic operation by automatic control performed by the mattress controller 42.

In the embodiment, the first sensor 31 is provided. The first sensor 31 is disposed under the mattress 76, for example. The first sensor 31 is configured to detect a biological signal including the body motion of the user of the mattress 76. The first sensor 31 outputs a signal SS corresponding to the biological signal. The mattress acquisition unit 43 acquires this signal SS. This signal SS is fed to the mattress controller 42. For example, the signal SS may include information on at least one of the breathing rate and the heart rate of the user. The signal SS may include information on a movement of at least one of the arms, the torso, and the feet of the user. The signal SS may include information on rolling over of the user. The signal SS may include information on the number of rolling over of the user.

The mattress controller 42 controls the state of the mattress 76 (such as the shape) according to a variation ΔS of the signal SS. This control is performed in such a way that the mattress controller causes the mattress drive unit 76f to control the pump unit 76b, for example. In this way, the mattress controller 42 is capable of performing automatic control based on the biological signal in addition to the manual control.

Hereinbelow, an example of the state of the mattress 76 is described.

Figure 9A:
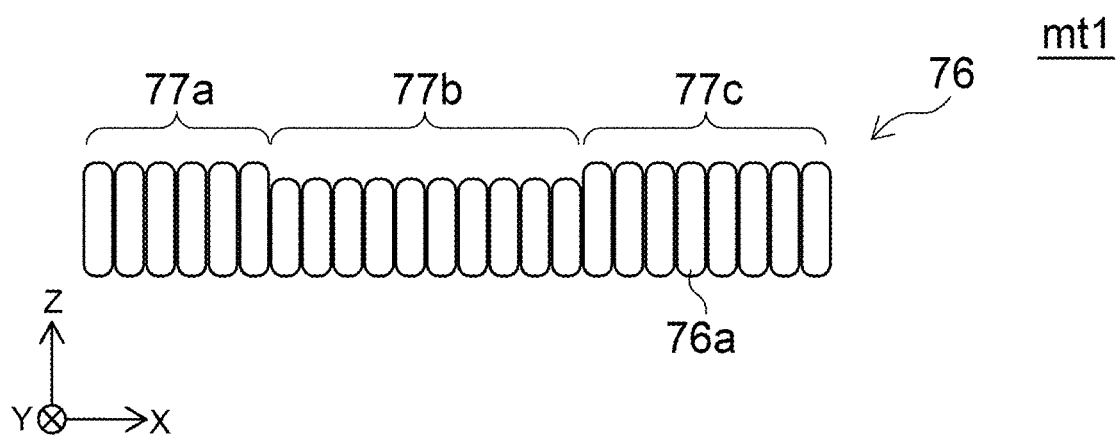
FIGS. 9A and 9B are schematic side views illustrating the mattress according to the embodiment.
Figure 9B:
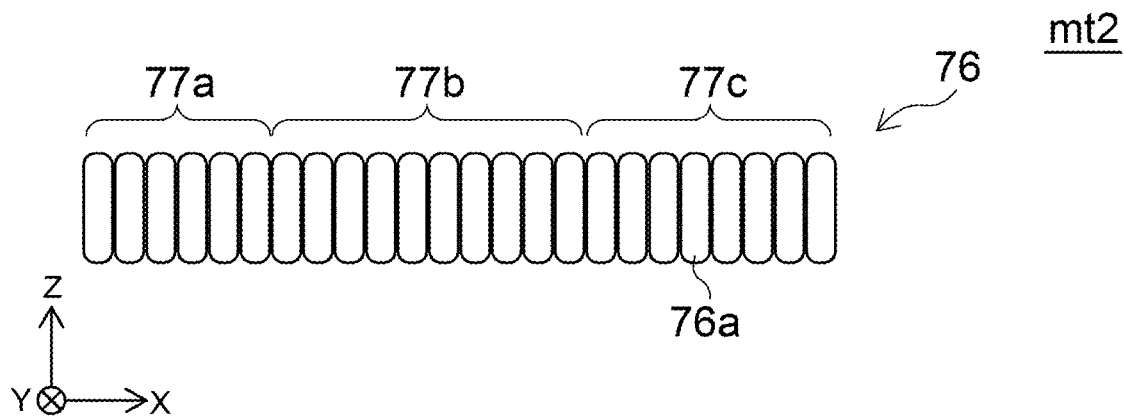

FIGS. 9A and 9B are schematic side views illustrating the mattress according to the embodiment.

Hereinbelow, the embodiment is described on the premise that the user is lying on the mattress illustrated in any of FIGS. 9A and 9B. The embodiment is described on the premise that the user's head is placed on the negative side of FIG. 9A in the X-axis direction and the user's feet are placed on the positive side of FIG. 9A in the X-axis direction.

FIGS. 9A and 9B illustrate the state of the mattress 76 (such as the shape). FIG. 9A corresponds to one state of the mattress 76 (a first mattress state mt1). FIG. 9B corresponds to the other state of the mattress 76 (a second mattress state mt2).

A part of the multiple air cells 76a (a head part 77a) corresponds to a head part of the user. Another part of the multiple air cells 76a (a waist part 77b) corresponds to a waist part of the user. Still another part of the multiple air cells 76a (a foot part 77c) corresponds to a foot part of the user.

As illustrated in FIG. 9A, in the first mattress state mt1, when the position of an upper surface of the head part 77a of the mattress 76 is used as a reference, the position of an upper surface of the waist part 77b of the mattress 76 is lower than the position of the upper surface of the head part 77a of the mattress 76. This means that the air cells in the waist part are so depressed that the inner pressure of the air cells in the waist part is lower than the inner pressure of the air cells on the head side, or means that the weight applied on the air cells in the waist part is larger than the weight applied on the air cells in the head part.

For example, the position of the upper surface of the waist part 77b of the mattress 76 is lower than the position of an upper surface of the foot part 77c of the mattress 76. In the first mattress state mt1, the mattress 76 has a gentle inclination. When the user lies on the mattress 76 in the first mattress state mt1, the back of the user is gently inclined. In the first mattress state mt1, the height of the foot part 77c may also be lower than the height of the head part 77a.

On the other hand, as illustrated in FIG. 9B, in the second mattress state mt2, the position of the upper surface of the waist part 77b of the mattress 76 is substantially equal to the position of the upper surface of the head part 77a of the mattress 76. The position of the upper surface of the waist part 77b of the mattress 76 is substantially equal to the position of the upper surface of the foot part 77c of the mattress 76. In the second mattress state mt2, the mattress 76 is substantially flat. When the user lies on the mattress 76 in the second mattress state mt2, the back of the user is substantially flat. In the second mattress state mt2, the position of the upper surface of the waist part 77b may be slightly higher than the position of the upper surface of the head part 77a.

For example, the gap between the position of the upper surface of the head part 77a of the mattress 76 and the position of the upper surface of the waist part 77b of the mattress 76 corresponds to the back angle θ.

For example, it is conceivable that the user can easily roll over when the mattress 76 is flat (e.g. in the second mattress state mt2). On the other hand, the user can easily fall asleep when the mattress 76 is gently inclined (e.g. in the first mattress state mt1).

In the embodiment, the mattress controller 42 changes the shape of the mattress 76 based on the biological signal of the user. For example, such change is constituted by switching between the first mattress state mt1 and the second mattress state mt2 described above. Thereby, it is possible to provide more comfortable sleep.

Hereinbelow, an example of the bed 70B including the mattress 76 is described.

Figure 10A:
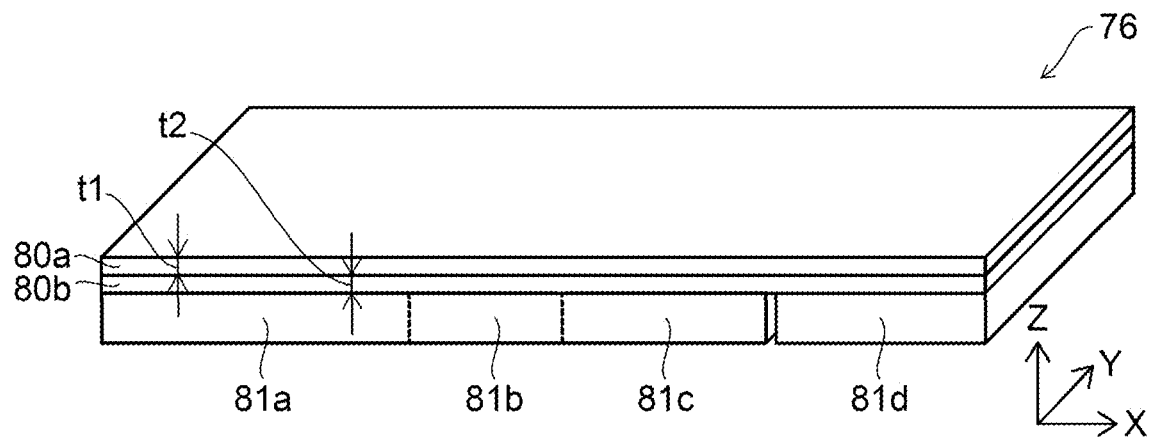
FIGS. 10A and 10B are schematic views illustrating the bed according to the first embodiment.
Figure 10B:
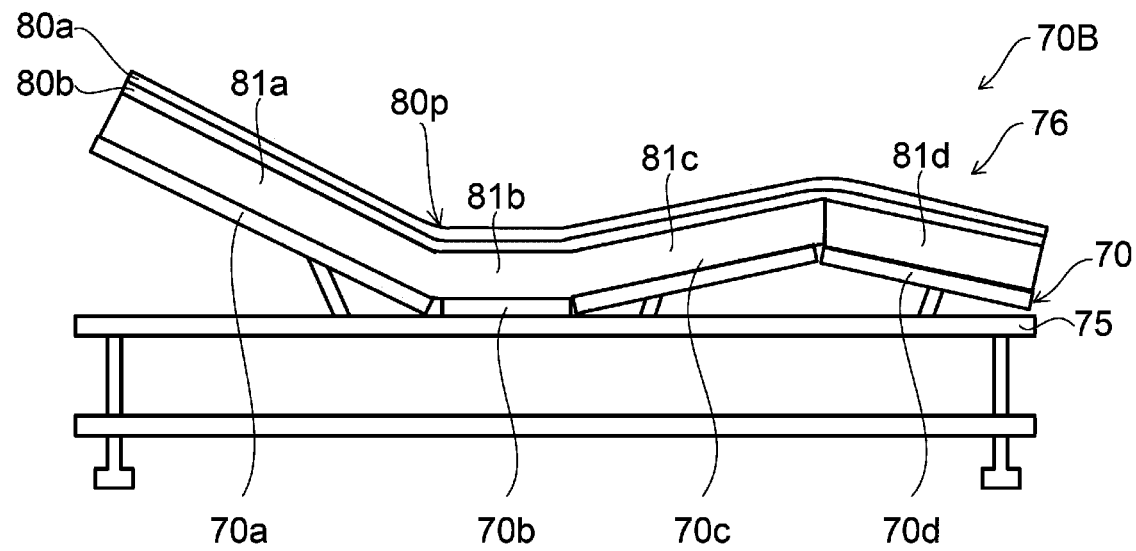

FIGS. 10A and 10B are schematic views illustrating the bed according to the first embodiment.

FIG. 10A is a perspective view illustrating the mattress 76. FIG. 10B is a sectional view illustrating the bed 70B including the mattress 76.

As illustrated in FIG. 10A, the mattress 76 includes multiple base sections (such as a first base section 81a and a second base section 81b), a first layer 80a, and a second layer 80b. In this example, the multiple base sections further include base sections 81c and 81d.

For example, the second layer 80b is provided on the multiple base sections, and the first layer 80a is provided on the second layer 80b.

The multiple base sections, the first layer 80a, and the second layer 80b include polymeric foam. The polymeric foam includes urethane foam, for example.

The multiple base sections may be side edge sections, for example. A central mattress section may be provided between the two side edge sections. As is to be described later, the central mattress section may include a gas housing body (e.g. air cell).

The multiple base sections are arranged in a first direction (e.g. the X-axis direction). For example, the direction from the first base section 81a to the second base section 81b extends in the first direction.

The Z-axis direction indicates a direction perpendicular to the X-axis direction. The Y-axis direction indicates a direction perpendicular to the X-axis direction and the Z-axis direction.

The first direction corresponds to a direction from the head to the feet of the user observed when the user sleeps on the mattress 76, for example. The Y-axis direction corresponds to the lateral direction. The Z-axis direction corresponds to a direction from a lower surface to an upper surface of the mattress 76.

As illustrated in FIG. 10A, for example, the direction from the first base section 81a to the second base section 81b (first direction) intersects with the direction from the first base section 81a to the first layer 80a (Z-axis direction) and intersects with the direction from the second base section 81b to the first layer 80a (Z-axis direction).

The second layer 80b is provided between the first base section 81a and the first layer 80a and between the second base section 81b and the first layer 80a. The second layer 80b is joined to the first layer 80a. The multiple base sections are joined to the second layer 80b. The second layer 80b is an intermediate layer, for example. In the embodiment, "joining" includes adhesive bonding and welding, for example.

As illustrated in FIG. 10B, the mattress 76 is placed on a bed section 70. The bed section 70 is an electric bed, for example. The bed section 70 includes the back section 70a, the seat section 70b, the upper leg section 70c, the lower leg section 70d, and the like, for example. These sections are supported on a frame 75, for example. The angle between these sections is adjustable.

The mattress 76 is placed on the bed section 70 having the above configuration. When the mattress 76 is placed on the bed section 70, the mattress 76 is transformed according to a change in the angle between the multiple sections. The mattress 76 is bent. In the embodiment, the first layer 80a and the second layer 80b have appropriate characteristics. This makes it possible to provide favorable comfort while inhibiting the multiple base sections from coming off from each other, breakage of the second layer 80b, and the like.

The first layer 80a and the second layer 80b each include multiple cells, for example. Each cell is an opening, for example. In one example, the size of each cell (opening) included in the second layer 80b is larger than the size of each cell (opening) included in the first layer 80*a*. An average size of cells included within a reference distance (e.g. 10 mm) may be used as the cell size. The size of each cell included in the second layer 80*b* is approximately 1 mm, for example. On the other hand, the size of each cell included in the first layer 80*a* is approximately 0.2 mm, for example. For example, the size of each cell included in the second layer 80*b* may be four times or more larger than the size of each cell included in the first layer 80*a*.

In one example, the number of cells in the second layer 80*b* is smaller than the number of cells in the first layer 80*a*. The number of cells is defined by "the number of cells" stated in JIS K6400-1: 2004 Appendix 1, for example. The number of cells corresponds to the number of cells existing within a reference distance. The number of cells in the second layer 80*b* is 22, for example. The number of cells in the first layer 80*a* is 50, for example. For example, the number of cells in the first layer 80*a* may be twice or more larger than the number of cells in the second layer 80*b*.

In one example, the tensile strength in the second layer 80*b* is larger than the tensile strength in the first layer 80*a*. The tensile strength in the second layer 80*b* is 150 kPa, for example. The tensile strength in the second layer 80*b* is preferably 140 kPa or larger, for example. On the other hand, the tensile strength in the first layer 80*a* is 30 kPa or larger and smaller than 140 kPa, for example. With the tensile strength described above, the mattress can achieve favorable cushioning characteristics while suppressing breakage and the like. The tensile strength is defined by the "tensile strength" stated in JIS K6400-5: 2012, for example. For example, the tensile strength in the second layer 80*b* may be 1.5 times or more larger than the tensile strength in the first layer 80*a*.

In one example, the stretchability in the second layer 80*b* is higher than the stretchability in the first layer 80*a*. The stretchability in the second layer 80*b* is 115%, for example. The stretchability in the first layer 80*a* is 80%, for example. The stretchability is defined by the "stretchability" stated in JIS K6400-5: 2012, for example. For example, the stretchability in the second layer 80*b* may be 1.2 times or more higher than the stretchability in the first layer 80*a*.

In the embodiment, the second layer 80*b* may have at least one of: the second cell having the second size larger than the first size of the first cell included in the first layer 80*a*; the number of second cells smaller than the number of first cells in the first layer 80*a*; the second tensile strength larger than the first tensile strength in the first layer 80*a*; and the second stretchability higher than the first stretchability in the first layer 80*a*.

In the embodiment, the first layer 80*a* is reinforced by the second layer 80*b* having the above configuration. Since the second layer 80*b* includes polymeric foam, the mattress can achieve favorable cushioning characteristics.

For example, as illustrated in FIG. 10B, when the mattress 76 is bent, strong stress is applied on a bent part (portion 80*p*). With the first layer 80*a* and the second layer 80*b* having the above configuration, it is possible to inhibit the multiple base sections from coming off from each other, breakage of the first layer 80*a* and the second layer 80*b*, and the like even when strong stress is applied on the bent part (portion 80*p*). According to the embodiment, it is possible to provide favorable comfort (e.g. softness) while inhibiting the multiple base sections from coming off from each other. For example, it is possible to provide favorable comfort (e.g. softness) while inhibiting breakage of the first layer 80*a* and the second layer 80*b* and the like.

In the embodiment, a thickness t2 of the second layer 80*b* (see FIG. 10A) is preferably 3 mm or larger. Thereby, the mattress can easily achieve favorable cushioning characteristics. A thickness t1 of the first layer 80*a* (see FIG. 10A) is preferably 3 mm or larger. Thereby, the mattress can easily achieve favorable cushioning characteristics.

By using polymeric foam for both of the first layer 80*a* and the second layer 80*b* (e.g. intermediate layer), it is possible to manufacture a mattress at low cost as compared to the case of using an urethane resin film (including cloth and the like, for example) as an intermediate layer.

Second Embodiment

Figure 11A:
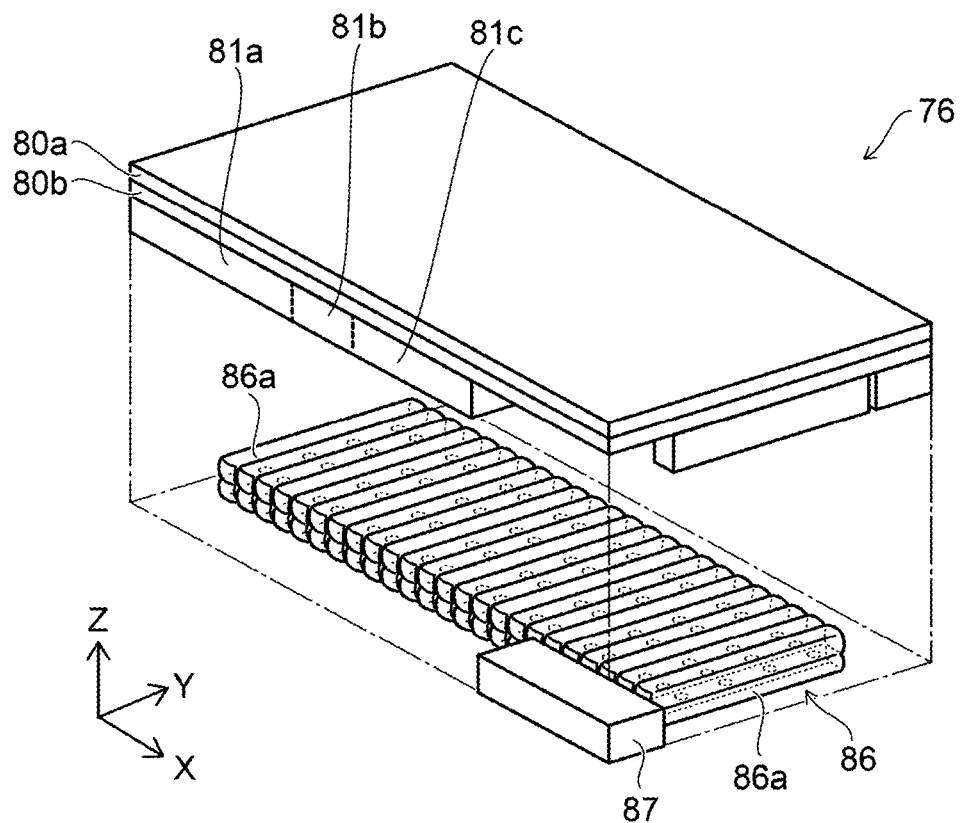
FIGS. 11A and 11B are schematic perspective views illustrating the mattress according to the second embodiment.
Figure 11B:
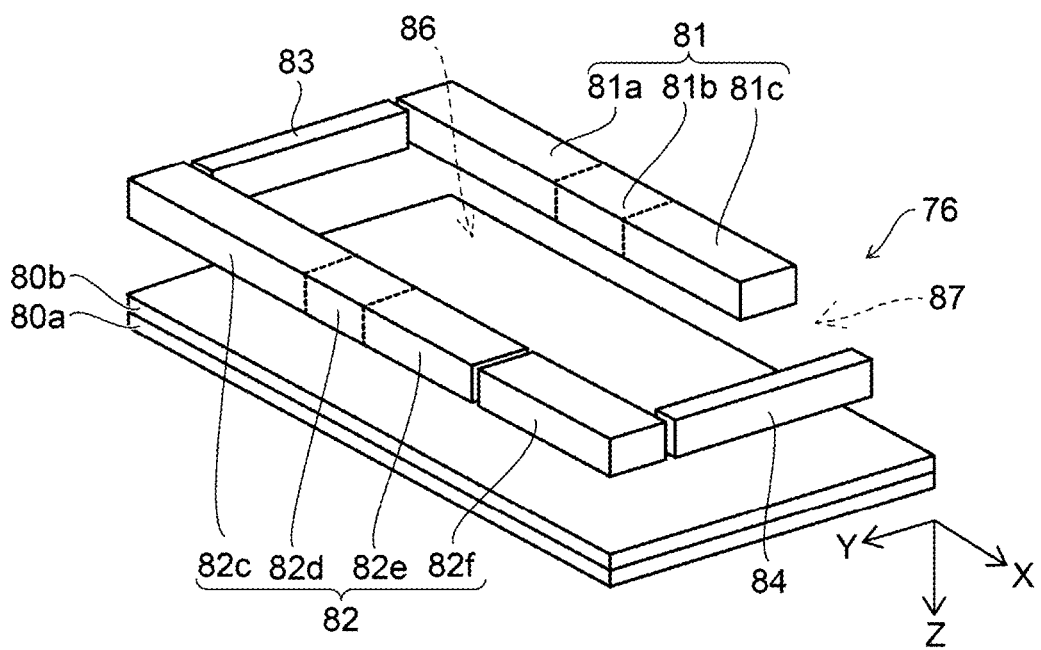

FIGS. 11A and 11B are schematic perspective views illustrating the mattress according to the second embodiment.

In these drawings, multiple constituents included in the mattress 76 according to the embodiment are illustrated separately from each other for the sake of viewability of the drawings. The Z-axis direction (e.g. vertical direction) illustrated in FIG. 11B is opposite the Z-axis direction illustrated in FIG. 11A.

As illustrated in FIGS. 11A and 11B, in addition to the first layer 80*a*, the second layer 80*b*, the first base section 81*a*, and the second base section 81*b*, the mattress 76 according to the embodiment further includes a third base section 82*c*, a fourth base section 82*d*, and a gas housing section 86. In this example, the mattress is further provided with a base section 82*e* and a base section 82*f*. The first base section 81*a* and the second base section 81*b* are included in a first side edge section 81, for example. The third base section 82*c*, the fourth base section 82*d*, the base section 82*e*, and the base section 82*f* are included in a second side edge section 82, for example.

The gas housing section 86 includes multiple gas housing bodies 86*a*. The direction from the first base section 81*a* to the gas housing section 86 (the Y-axis direction in this example) intersects with the direction from the first base section 81*a* to the first layer 80*a* (e.g. the Z-axis direction). The direction from the second base section 81*b* to the gas housing section 86 (the Y-axis direction in this example) intersects with the direction from the second base section 81*b* to the first layer 80*a* (e.g. the Z-axis direction). The direction from the gas housing section 86 to the first layer 80*a* extends along the direction from the first base section 81*a* to the first layer 80*a* (e.g. the Z-axis direction).

As illustrated in FIG. 11B, the direction from the third base section 82*c* to the fourth base section 82*d* intersects with the direction from the first base section 81*a* to the first layer 80*a* (e.g. the Z-axis direction). The direction from the third base section 82*c* to the fourth base section 82*d* extends along the X-axis direction.

The direction from the third base section 82*c* to the first layer 80*a* extends along the direction from the first base section 81*a* to the first layer 80*a* (the Z-axis direction). The direction from the fourth base section 82*d* to the first layer 80*a* extends along the direction from the first base section 81*a* to the first layer 80*a* (the Z-axis direction).

The gas housing section 86 is located between the first base section 81*a* and the third base section 82*c* in the Y-axis direction. The gas housing section 86 is located between the second base section 81*b* and the fourth base section 82*d* in the Y-axis direction.

The second layer 80*b* is provided between the third base section 82*d* and the first layer 80*a* and between the fourth base section 82*d* and the first layer 80*a*.

The mattress 76 may further include a pump unit 87. The pump unit 87 is configured to supply and discharge gas to and from the multiple gas housing bodies 86a. A part of the gas housing section 86 may be provided between the pump unit 87 and the base section 82f.

The first side edge section 81 and the second side edge section 82 make it possible to inhibit the multiple base sections from coming off from each other, breakage of the first layer 80a and the second layer 80b, and the like.

As illustrated in FIG. 11B, the mattress may be provided with edge sections 83 and 84. The edge sections 83 and 84 include polymeric foam. The gas housing section 86 is provided between the edge section 83 and the edge section 84 in the first direction (the X-axis direction). Owing to the edge section 83, the shape of the mattress can be kept properly in an edge section thereof on the side of the head part of the user. Owing to the edge section 84, the shape of the mattress can be kept properly in an edge section thereof on the side of the foot part of the user. The base sections included in the mattress according to the embodiment may be cut at least partially.

Hereinbelow, some examples of the first sensor 31 are described.

Figure 12A:
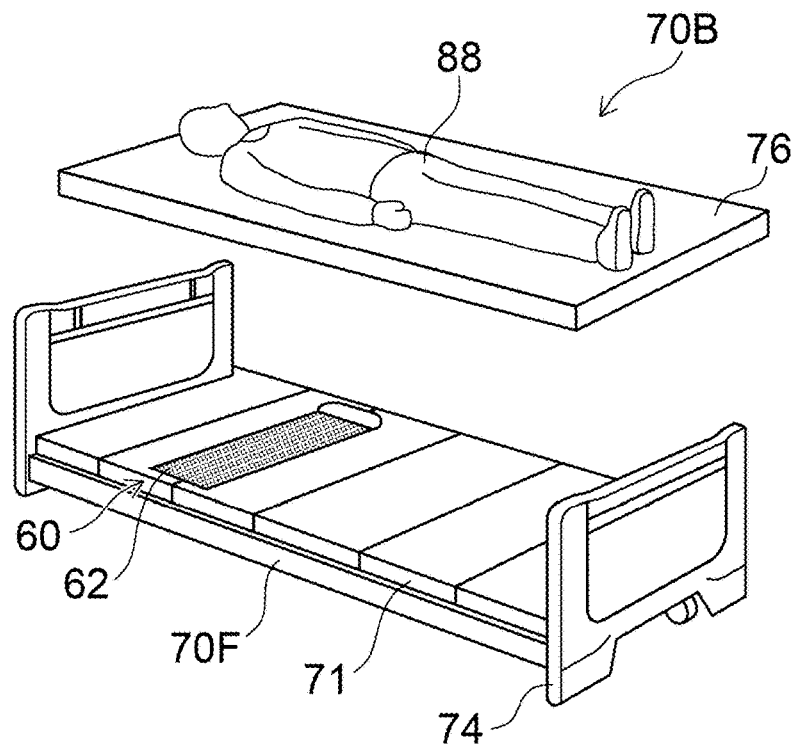
FIGS. 12A and 12B are schematic views illustrating the bed according to the embodiment.
Figure 12B:
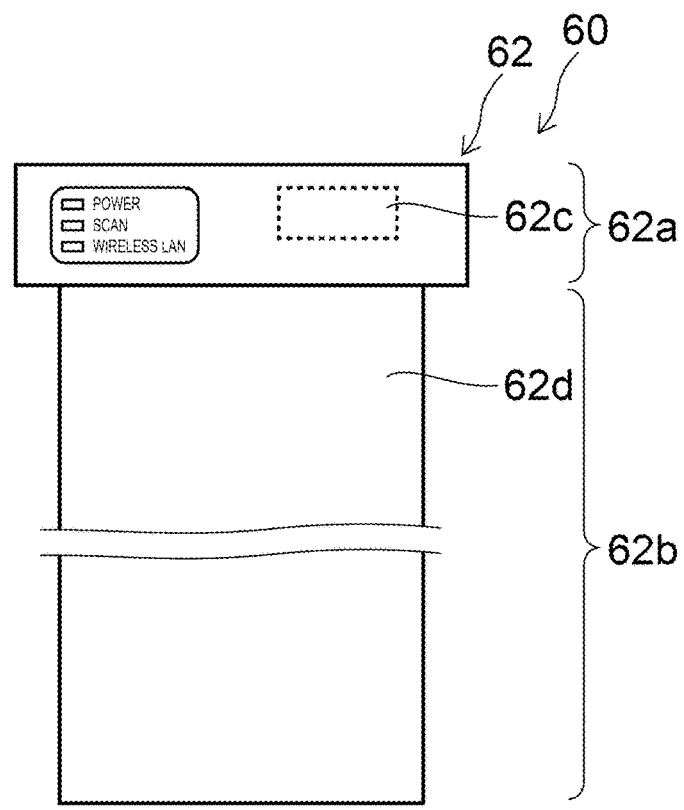

FIGS. 12A and 12B are schematic views illustrating the bed according to the embodiment.

FIG. 12A is a schematic perspective view illustrating a sensor 62 and the layout of the sensor 62. FIG. 12B is a schematic plan view illustrating the sensor 62. In FIG. 12A, constituents are illustrated separately from each other for the sake of viewability of the drawings. The sensor 62 is one example of the first sensor 31.

As illustrated in FIG. 12A, the frame 70F is supported on a bed leg section 74. A section 71 (such as the back section 70a, the seat section 70b, the upper leg section 70c, and the lower leg section 70d) is provided on the frame 70F. The mattress 76 is provided on the section 71. A user 88 lies on the mattress 76. The sensor 62 is provided between the section 71 and the mattress 76, for example. In this example, the sensor 62 is sheet-shaped or plate-shaped.

As illustrated in FIG. 12B, the sensor 62 includes a circuit unit 62a and a sensor unit 62b. The circuit unit 62a includes a communication unit 62c. The communication unit 62c is configured to transmit and receive data to and from the controller 40. The communication unit executes such data exchange by any method including at least one of wired and wireless methods.

The sensor unit 62b includes a sensor device 62d, for example. The sensor unit 62b is configured to detect a force (or characteristics corresponding to the force) received by the sensor unit 62b. The force includes at least one of pressure and sound wave, for example. The sensor unit 62b includes a pressure sensor, for example. The sensor unit 62b includes a microphone, for example.

The force (at least one of pressure and sound wave) charged by the user 88 is applied on the sensor unit 62b via the mattress 76. The force is generated based on the body motion, for example. For example, a signal generated based on the force detected by the sensor unit 62b is output from the circuit unit 62a. In one example, the circuit unit 62a may analyze the signal generated based on the force detected by the sensor 62b. In this case, the circuit unit 62a may presume the condition of the user 88 (e.g. whether the user is away from the bed, is sleeping, or awakes) based on at least one of the magnitude of the signal (force) generated based on the force detected by the sensor unit 62b and a temporal change in the magnitude of the signal (force).

In one example, the signal generated based on the force detected by the sensor unit 62b may be fed to the controller 40 from the circuit unit 62a. The controller 40 presumes the condition of the user 88 (e.g. whether the user is away from the bed, is sleeping, or awakes) based on at least one of the magnitude of the signal (force) and a temporal change in the magnitude of the signal (force). Alternatively, the circuit unit 62a may presume the condition of the user 88 (e.g. whether the user is away from the bed, is sleeping, or awakes) based on at least one of the force detected by the sensor unit 62b and a temporal change in the force. The condition of the user 88 may include the condition of getting up, preparing for moving away from the bed (such as being in a sitting position with his/her soles of feet on the floor), being away from the bed, falling asleep, sleeping, and being awake.

At least one of the controller 40 and the circuit unit 62a detects the biological signal of the user 88 based on at least one of the magnitude of the signal (force) and a temporal change in the magnitude of the signal (force). The biological signal includes at least one of the breathing rate and the heart rate of the user 88. The sleeping condition may be presumed based on the biological signal. The posture of the user 88 during sleeping may be presumed based on the biological signal.

For example, vibration generated according to the condition of the user 88 is applied on the sensor unit 62b. The vibration is generated according to the body motion of the user 88, for example. The vibration is detected by the sensor unit 62b. The vibration may include sound.

For example, vibration detection means (the sensor unit 62b) and a processor (at least a part of at least one of the circuit unit 62a and the controller 40) are provided. The processor includes a computer, for example. The vibration detection means is configured to detect the vibration of the user 88 on the bed 70B, for example. The processor includes activity amount calculation means, sleeping judgment value calculation means, and sleeping condition judgment means, for example. These means are classified by their functions. The activity amount detection means is configured to calculate the amount of activity of a person sleeping per sampling unit time based on the vibration detected by the vibration detection means, for example. The sleeping judgment value calculation means is configured to calculate, as a sleeping judgment value, the sum of values respectively obtained by multiplying the amount of activity at a first time point (e.g. the current time) and the amount of activity calculated at a second time point (e.g. a time point prior to the current time) by correction coefficients obtained by weighting according to the time, for example. The sleeping condition judgment means is configured to judge that the user is awake if the sleeping judgment value exceeds a predetermined threshold and judge that the user is sleeping if not.

FIGS. 13A to 13D are schematic views illustrating the bed according to the embodiment.

Figure 13A:
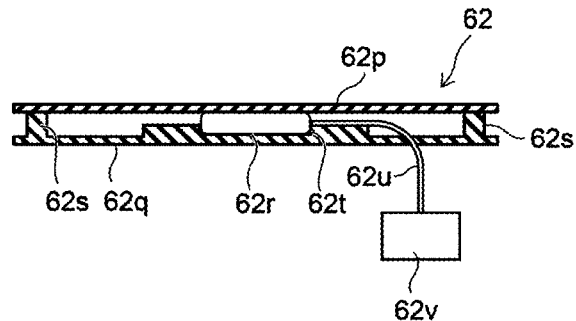
FIGS. 13A to 13D are schematic views illustrating the bed according to the embodiment.
Figure 13B:
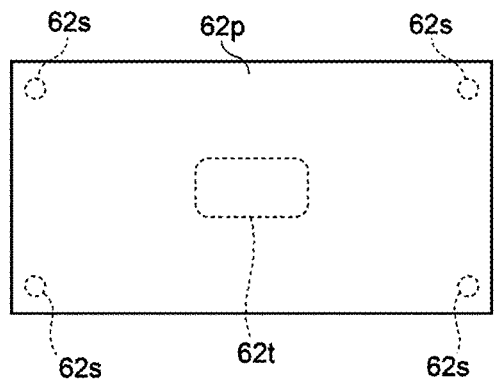
Figure 13C:
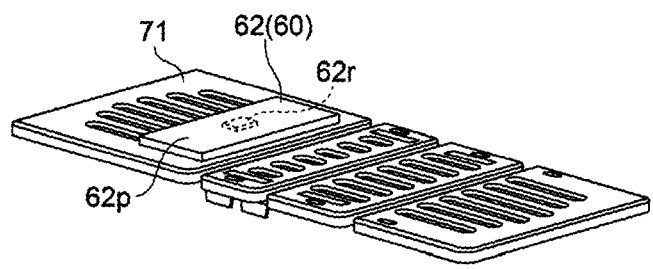
Figure 13D:
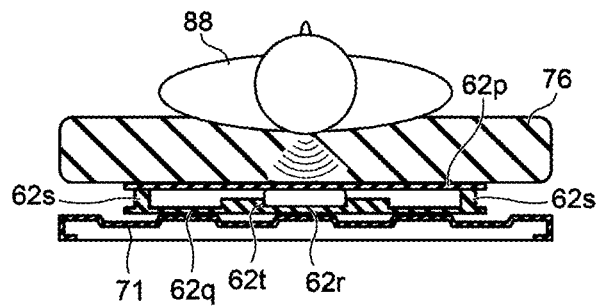

FIG. 13A is a sectional view of an example of the sensor 62. FIG. 13B is a plan view of the example of the sensor 62. FIG. 13C is a perspective view illustrating the layout of the sensor 62. FIG. 13D is a side view illustrating the layout of the sensor 62.

As illustrated in FIG. 13A, in this example, the sensor 62 includes a first platy body 62p and a second platy body 62q. The second platy body 62q is opposed to the first platy body 62p. These platy bodies may be sheet-shaped.

The second platy body 62q includes support protrusions 62s. The support protrusions 62s are opposed to an outer edge part of the first platy body 62p. The first platy body 62p includes an inner part located inside the outer edge part. An air housing body 62r is provided between the inner part and the second platy body 62q. In this example, the second platy body 62q is provided with a groove 62t. The air housing body 62r is provided inside a space formed by (a space sectioned by) the groove 62t. One end of a signal line 62u is connected to the air housing body 62r. The other end of the signal line 62u is connected to a detection circuit 62v (detection device).

As illustrated in FIG. 13B, the support protrusions 62s are opposed to a part of outer edges of the first platy body 62p. In this example, the support protrusions 62s are arranged at four corner parts of the first platy body 62p. The sensor 62 is sheet-shaped or plate-shaped.

As illustrated in FIG. 13C, the above sensor 62 is placed on the section 71. As illustrated in FIG. 13D, the sensor 62 is placed on the section 71, and the mattress 76 is placed thereon. The user 88 lies on the mattress 76.

For example, a force generated according to the body movement of the user 88 is applied on the air housing body 62r. The force includes vibration, for example. The force (or characteristics corresponding to the force) applied on the air housing body 62r is detected by the detection circuit 62v. For example, a pressure detector is provided in the air housing body 62r, and a signal (detection result) acquired by the pressure detector is fed to the detection circuit 62v. For example, a microphone is provided in the air housing body 62r, and a signal (detection result) acquired by the microphone is fed to the detection circuit 62v. For example, an output (signal) from the detection circuit 62v is fed to the controller 40. The controller 40 presumes the condition of the user 88 (e.g. whether the user is away from the bed, is sleeping, or awakes). Alternatively, the detection circuit 62v may presume the condition of the user 88 (e.g. whether the user is away from the bed, is sleeping, or awakes) based on at least one of the detected force and a temporal change in the force. The condition of the user 88 may include the condition of getting up, being in a sitting position with his/her soles of feet on the floor (such as preparing for moving away from the bed), being away from the bed, falling asleep, sleeping, and being awake.

The sensor 62 is a biological information collection device, for example. In the sensor 62, the first platy body 62p is disposed on the user 88's body side, for example. The second platy body 62q is provided on the support side, for example. The transformable air housing body 62r for detecting air pressure is provided between central parts of the first platy body 62p and the second platy body 62q. The groove 62t for mounting the air housing body 62r therein is provided in the central part of the second platy body 62q. The support protrusions 62s protrude in a direction from the second platy body 62q to the first platy body 62p. The support protrusions 62s support the circumferential four corners of the first platy body 62p. The support protrusions 62s are designed to constantly support the first platy body 62p in a horizontal state (normal state).

In the embodiment, the sensor 62 can be modified in various ways.

Figure 14:
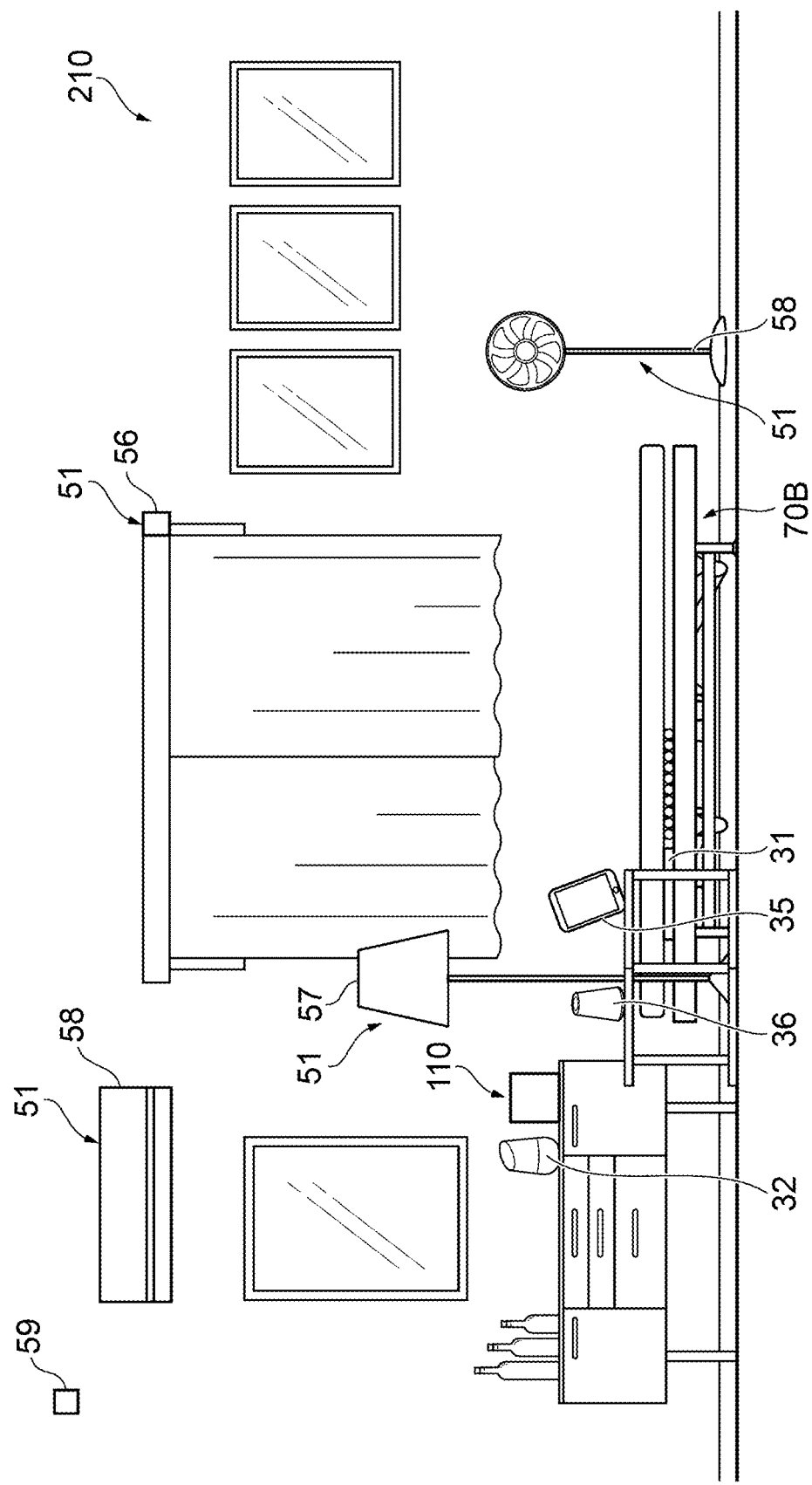
FIG. 14 is a schematic view illustrating a bed system according to the embodiment.

FIG. 14 is a schematic view illustrating the bed system according to the embodiment.

As illustrated in FIG. 14, the bed system 210 includes the bed 70B and the control apparatus 110. The bed system 210 may include at least one of the first sensor 31, the second sensor 32, the electronic device 35, the sound device 36, the environment controller 51, the dimmer 56, the lighting device 57, the blower 58, and the display device 59.

Figure 15:
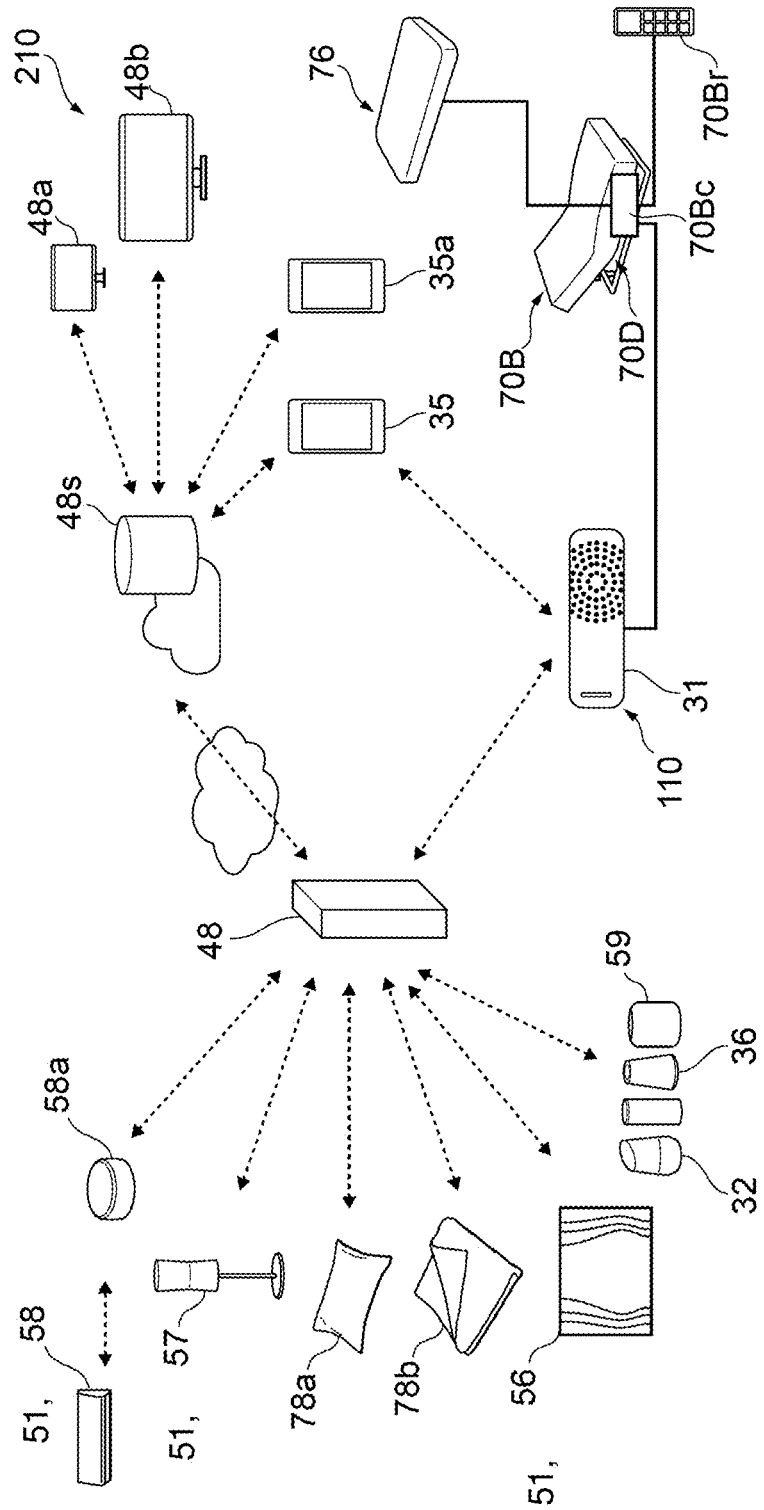
FIG. 15 is a schematic view illustrating the bed system according to the embodiment.

FIG. 15 is a schematic view illustrating the bed system according to the embodiment.

As illustrated in FIG. 15, the bed system 210 is provided with the bed 70B and the control apparatus 110. In this example, at least a part of the function of the control apparatus 110 is implemented by at least a part of a controller included in the first sensor 31. The bed 70B may include a bed controller 70Bc. The bed controller 70Bc is configured to control the drive unit 70D. The bed 70B may include a bed reception unit 70Br. The bed reception unit 70Br is configured to receive manipulation regarding the bed 70B. The bed reception unit 70Br is a remote controller, for example. The bed 70B may include the mattress 76. In the case where the mattress 76 is an air mattress, the pressure of the air cells 76a may be controlled by the bed controller 70Bc. Data exchange between the control apparatus 110 and the bed 70B may be executed by any of wired and wireless methods.

The bed system 210 may be provided with a communication device 48. The communication device 48 is a router, for example. The communication device 48 may perform communication via wireless LAN (local area network). For example, the control apparatus 110 and other devices communicate with each other via the communication device 48.

Other devices include at least one of the second sensor 32, the sound device 36, the display device 59, and the environment controller 51, for example. The environment controller 51 includes at least one of the dimmer 56 (such as a curtain), the lighting device 57, and the blower 58, for example. The communication device 48 and the blower 58 (such as an air conditioner) may communicate with each other via a relay device 58a. The relay device 58a may be a remote controller for the blower 58 (such as an air conditioner).

Other devices may include bed accessories 78a and 78b and the like. The bed accessory 78a is a pillow, for example. The bed accessory 78b is an electric blanket, for example. For example, the control apparatus 110 may control the height, the temperature, or the like of the pillow. For example, the control apparatus 110 may control the temperature of the electric blanket or the like. For example, the control apparatus 110 may control at least one of the temperature of the bed 70B, the temperature of the mattress 76, and the temperature of the room. Such temperature control may be executed according to the body temperature of the user. The shape of the pillow may be controlled suitably and customizable according to the shape of the head of the user. This suppresses a stiff shoulder and the like, for example. For example, when the user starts snoring, the shape of the pillow may be changed to stop snoring.

The communication device 48 and other devices described above communicate with each other via wireless LAN or the like, for example.

Data acquired by the first sensor 31 may be fed to a server 48s via the communication device 48. The server 48s is capable of communicating with any electronic device. For example, the electronic device includes the electronic device 35 for the user 88, an electronic device 35a for a carer, an administrative computer 48a, any computer 48b, and the like.

At least a part of the function of the control apparatus 110 is implemented by at least a part of the controller included in the first sensor 31. At least a part of the function of the control apparatus 110 may be implemented by at least a part of the bed controller 70Bc. At least a part of the function of the control apparatus 110 may be executed by the electronic device 35 or an electronic device 35s. At least a part of the function of the control apparatus 110 may be implemented by at least one of the server 48s, the administrative computer 48a, and the computer 48b. At least a part of the control apparatus 110 may be included in the first sensor 31, the bed controller 70Bc, the electronic device 35, the electronic device 35s, the server 48s, the administrative computer 48a, and the computer 48b.

According to the embodiment, it is possible to provide the control apparatus which is capable of providing high quality sleep.

The embodiments have been described above while referring to the concrete examples. However, this disclosure is not limited to these concrete examples. For example, concrete configurations of constituents, such as the acquisition unit and the controller, included in the control apparatus are contained in the scope of this disclosure as long as those skilled in the art can implement this disclosure in the same manner as above and achieve the same effect as above by making selection properly from the publicly known scope.

Any combination of two or more constituents of the concrete examples within a technically possible scope is also included in the scope of this disclosure as long as it contains the gist of this disclosure.

In addition, all control apparatuses that those skilled in the art can implement by changing the design as appropriate based on the control apparatus described above as the embodiments also fall within the scope of this disclosure as long as they contain the gist of this disclosure.

Further, those skilled in the art can conceive of various modification examples and revision examples within the idea of this disclosure, and such modification examples and revision examples are also recognized as falling within the scope of this disclosure.

While the several embodiments have been described, these embodiments are provided as examples and are not for limiting the scope of this disclosure. These embodiments can be implemented in various modes other than those described above, and various omissions, replacements, and changes can be made without departing from the gist of this disclosure. These embodiments and their modifications are included in the scope and gist of this disclosure, and are included in the scope of the subject matters described in the scope of claims and their equivalents.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An apparatus comprising:
   an acquisition unit configured to acquire first information from a first sensor, the first information including biological information of a user of a bed, and the bed including a back section; and
   a controller configured to predict a time the user is expected to wake up from sleep based on the first information, a condition of expected to wake up indicating the condition during which the user is not awake but is likely to wake up,
   wherein the controller is configured to
   perform, based on the time the user is to wake up, an operation of increasing an angle of the back section and at least one of
   an operation of increasing lightness at a location of the bed, or
   an operation of sending wind toward the bed,
   increase the angle of the back section with respect to a horizontal plane of the bed after performing the at least one of the operation of increasing lightness at the location of the bed or the operation of sending wind toward the bed based on the first information including information indicating that the user is in a lateral position,
   increase the angle of the back section with respect to a horizontal plane of the bed by a first amount based on the first information including information indicating that the user is in a prone position, and
   increase the angle of the back section with respect to the horizontal plane by a second amount, larger than the first amount, based on the first information including information indicating that the user is in a supine position.

2. The apparatus according to claim 1, wherein, the controller is configured to increase the angle of the back section before performing the at least one of the operation of increasing lightness or the operation of sending wind toward the bed based on the first information including information indicating that the user is in the supine position.

3. The apparatus according to claim 1, wherein
   the acquisition unit is configured to further acquire information on lightness at the location of the bed, and
   the controller is configured to increase the angle of the back section with respect to the horizontal plane of the bed at the time the user is to wake up based on the lightness at the location being greater than or equal to a threshold and the first information including information indicating that the user is in the prone position.

4. The apparatus according to claim 3, wherein
   the controller is configured to increase the lightness at the location of the bed when the user is to wake up based on the lightness at the location being smaller than the threshold.

5. The apparatus according to claim 1, wherein,
   the controller is configured to increase the lightness at the location of the bed by at least one of an operation of irradiating the location of the bed with light or an operation of opening a dimmer located in a room where the bed is placed.

6. The apparatus according to claim 1, wherein
   the first sensor is configured to presume whether the user is sleeping or awakes, and
   the controller is configured to control a display device to display the condition that the user is sleeping or that the user awakes thus presumed.

7. The apparatus according to the claim 1, wherein the acquisition unit is configured to further acquire information on whether the user manipulates any devices, and
   wherein the controller is configured to perform an operation changing the angle of the back section based on the user not manipulating any devices.

8. The apparatus according to claim 7, wherein
   the controller is configured not to perform an operation changing the angle of the back section based on the user manipulating any devices.

9. The apparatus according to claim 1, wherein the acquisition unit is configured to further acquire sound, and wherein the controller is configured to perform an operation changing the angle of the back section based on the acquisition unit detecting a snoring sound.

10. The apparatus according to claim 9, wherein the controller is configured to perform an operation increasing the angle of the back section based on the acquisition unit detecting the snoring sound.

11. The apparatus of claim 1, wherein
the biological information includes at least one of a heart rate, a respiratory rate or a body movement of the user, and
the controller is configured to determine the time the user is to wake up based on a change of the at least one of the heart rate, the respiratory rate, or the body movement of the user.

12. The apparatus of claim 11, wherein the controller is configured to determine the time the user is to wake up based on the change of the at least one of the heart rate, the respiratory rate, or the body movement of the user and a current time.

13. The apparatus of claim 11, wherein
the controller is configured to determine a cycle of a REM state and a non-REM state of the user based on the change of the at least one of the heart rate, the respiratory rate, or the body movement of the user, and
the controller is configured to determine the time the user is to wake up based on the cycle of the REM state and the non-REM state of the user.

14. The apparatus of claim 1, wherein the controller is configured to predict the time the user is to wake up based on the first information and whether a current time is within a threshold amount of time from a preset wake-up time.

* * * * *